United States Patent [19]

Renzoni et al.

[11] Patent Number: 5,135,717
[45] Date of Patent: Aug. 4, 1992

[54] TETRABENZTRIAZAPORPHYRIN REAGENTS AND KITS CONTAINING THE SAME

[75] Inventors: George E. Renzoni; Deborah C. Schindele; Louis J. Theodore, all of Seattle, Wash.; Clifford C. Leznoff, North York, Canada; Karen L. Fearon, Woodinville; Barry V. Pepich, Seattle, both of Wash.

[73] Assignee: British Technology Group USA Inc., Gulph Mills, Pa.

[21] Appl. No.: 398,433

[22] Filed: Aug. 29, 1989

Related U.S. Application Data

[63] Continuation-in-part of Ser. No. 241,608, Sep. 8, 1988, abandoned, and a continuation-in-part of Ser. No. 366,971, Jun. 14, 1989, which is a continuation-in-part of Ser. No. 3,226, Nov. 12, 1987, which is a continuation-in-part of Ser. No. 61,937, Jun. 12, 1987, abandoned, and a continuation-in-part of Ser. No. 946,475, Dec. 24, 1986, Pat. No. 4,803,170.

[51] Int. Cl.$^5$ .............................................. G01N 33/58
[52] U.S. Cl. .................................... 422/61; 435/5; 435/6; 435/7.1; 435/29; 435/810; 435/975; 436/94; 436/172; 436/501; 436/546; 436/808; 530/345; 536/18.7; 536/27; 540/121; 540/128; 540/139; 540/140
[58] Field of Search .................. 128/24.1; 422/61; 436/94, 172, 501, 506, 510, 512, 513, 536, 546, 808; 435/5-7, 29, 810, 7.1, 975; 530/345; 536/18.7, 27; 540/121, 128, 129-132, 135, 139, 140

[56] References Cited

U.S. PATENT DOCUMENTS 2,122,137 6/1938 Gassner et al. ............... 260/12
2,124,299 7/1938 Holzach et al. ............... 260/12

(List continued on next page.)

FOREIGN PATENT DOCUMENTS 252683 1/1988 European Pat. Off. .
WO88/04777 6/1988 PCT Int'l Appl. .

OTHER PUBLICATIONS

Prober, J. M., et al., A system for rapid DNA sequencing with fluorescent chain-terminating dideoxynucleotides, *Science* 238:336–341, Oct. 16, 1987.
Hale, P. D. et al., On the electronic structure of substituted phthalocyanines: a Hartree–Fock–Slater study of octacyano- and octafluoro-substituted (phthalocyaninato)silicon dihydroxide, *J. Am. Chem. Soc.* 109(20):5943–5947, 1987.

(List continued on next page.)

Primary Examiner—Robert J. Hill, Jr.
Attorney, Agent, or Firm—Christensen, O'Connor, Johnson & Kindness

[57] ABSTRACT

Red-shifted, water-soluble, fluorescent, monomerically-tetherable derivatives having the formula:

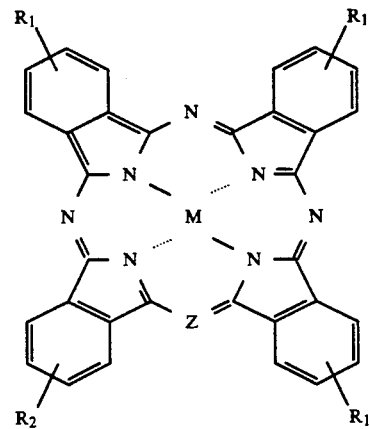

wherein, M represents either $H_2$ or is selected from among the following metals: aluminum, silicon, phosphorus, gallium, germanium, cadmium, scandium, magnesium, tin, and zinc. Each $R_1$ is independently selected from —XYW, —YW, and —W. X represents either a carbon, or heteroatom selected from among oxygen, nitrogen, sulfur, phosphorus, silicon, and selenium; Y represents a linking group; and W represents a water solubilizing group. The substituent $R_2$ is selected from among —A, —Y'A, —XA, and —XY'A, where A denotes a biological entity such as an antibody, antibody fragment, nucleotide, nucleic acid probe, antigen, oligonucleotide, deoxynucleotide, dideoxynucleotide, avidin, streptavidin or membrane probe, or $R_2$ is a reactive or activatable group suitable for conjugating to a biological entity. Y' is a linking group that tethers the biological entity to the phthalocyanine or tetrabenztriazaporphyrin macrocycle. Z is either a nitrogen atom or a carbon substituted with hydrogen, alkyl, aryl, or aralkyl groups. Z may also be attached to $R_2$. Also disclosed are derivatives of the compounds of the above formula in which 1–4 of the benzo rings(s) contain 1 or 2 N atoms. Methods of sequencing DNA and detecting analytes, including cells, using these derivatives are disclosed, as are kits for carrying out assays for the analytes and flow cytometry. Methods of detecting DNA using cationic compounds of the above formula, wherein $R_2=R_1$ and $W=-N^+D_1D_2D_3$ are also disclosed. Further, compounds containing Tc, Gd, etc. as the metal in the above formula may be used for imaging or therapy.

16 Claims, 18 Drawing Sheets

U.S. PATENT DOCUMENTS

| | | | |
|---|---|---|---|
| 2,456,274 | 12/1948 | Gutzwiller et al. | 260/314.5 |
| 2,525,620 | 10/1950 | Scalera et al. | 260/465 |
| 2,525,621 | 10/1950 | Scalera et al. | 260/465 |
| 4,803,170 | 2/1989 | Stanton et al. | 436/518 |
| 4,833,332 | 5/1989 | Robertson, Jr. et al. | 250/458.1 |

OTHER PUBLICATIONS

Derkacheva, V. M., and E. A. Luk'yanets, Phthalocyanines and related compounds, XVIII. Phenoxy- and (phenylthio)-substituted phthalocyanines, *J. Gen. Chem. USSR* 50:1874–1878, 1980.

Brannon, J. H., and D. Magde, Picosecond laser photophysics. Group 3A phthalocyanines, *J. Am. Chem. Soc.* 102(1):62–65, 1980.

Ben-Hur, E., and I. Rosenthal, Photosensitized inactivation of Chinese hamster cells by phthalocyanines, *Photochem. Photobiol.* 42(2):129–133, 1985.

Barrett, P. A. et al., Phthalocyanines and related compounds. Part XV. Tetrabenztriazaporphin: its preparation from phthalonitrile and a proof of its structure, *J. Chem. Soc.* 1809–1828, 1939.

Solovev, K. N. et al., Influence of AZO-substitution on the spectral-luminescent properties of benzoporphyrins, *Opt. Spectrosc.* 27:24–29, 1969.

Leznoff, C. C. et al., Metallophthalocyanine dimers incorporating five-atom covalent bridges, *Can. J. Chem.* 63:623–631, 1985.

Rosenthal, I. et al., The effect of substituents on phthalocyanine photocytotoxicity, *Photochem. Photobiol.* 46(6):959–963, 1987.

Witkiewicz, Z. et al., Properties of octamethoxyphthalocyanines. I. On their syntheses, electrical conductivity, and catalytic activity, *Materials Science II* 1:39–45, 1976.

Metz, J. et al., Synthesis and properties of substituted (phthalocyaninato)iron and -cobalt compounds and their pyridine adducts, *Inorg. Chem.* 23:1065–1071, 1984.

Oksengendler, I. G. et al., Trifluoromethylthio- and trifluoromethylsulfonyl-substituted phthalocyanines, *J. Org. Chem. USSR* 14(5):1046–1051, 1978.

Vogler, A. and H. Kunkely, Template synthesis and optical spectra of Zinc-2,3-naphthalocyanine, *Inorganica Chimica Acta* 44:L209–L210, 1980.

Lindstead, R. P. et al., Phthalocyanines. Part IX. Derivatives of thiophen, thionaphthen, pyridine, and pyrazine, and a note on the nomenclature, *J. Chem. Soc.* 911–922, 1937.

Spikes, J. D., Phthalocyanines as photosensitizers in biological systems and for the photodynamic therapy of tumors, *Photochem. Photobiol.* 43(6):691–699, 1986.

Ueda, K-i, and T. Hasiguchi, A new route to tetrafluorophthalonitrile and tetrafluoroterephthalonitrile, *Bull. Chem. Soc. Jpn.* 40(3):690–691, 1967.

Mikhalenko, S. A., and E. A. Luk'yanets, Phthalocyanines and related compounds. I. Synthesis and properties of tetraphenylphthalocyanines, *J. Gen. Chem. USSR* 39:2081–2086, 1969.

Mikhalenko, S. A., and E. A. Luk'yanets, Dimethylamino-substituted phthalocyanines, *J. Gen. Chem. USSR* 46:2075, 1976.

Rousseau, J. et al., Synthesis, tissue distributed and tumor uptake of [99-Tc]tetrasulfophthalocyanine, *Int. J. Appl. Radiat. Istot.* 34:571–579, 1983.

Smith, L. M. et al., The synthesis of oligonucleotides containing an aliphatic amino group at the 5' terminus: synthesis of fluorescent DNA primers for use in DNA sequence analysis, *Nucleic Acids Research* 13(7):2399–2412, 1985.

Clark, J. H. et al., Fluorodenitrations using tetrabutylammonium fluoride, *Tetrahedron Letters* 26(18):2233–2236, 1985.

Smith, L. M., DNA sequence analysis: past, present, and future, *ABL*, pp. 10–25, May 1989.

Leznoff, C. et al., Synthesis and photocytotoxicity of some new substituted phthalocyanines, *Photochemistry and Photobiology*, 49(3):279–284, 1989.

Leznoff, C. et al., "Preparation of substituted tetrabenzotriazaporphyrins and a tetranaphthotriazaporphyrin: A route to mono-meso-substituted phthalocyanine analogues," *J. Org. Chem.* 55:2186–2190 (1990).

Wohrle, D. et al., "Synthesis of positively charged phthalocyanines and their activity in the photodynamic therapy of cancer cells," *Photochemistry and Photobiology*, 51(3):351–356 (1990).

TETRABENZTRIAZAPORPHYRIN REAGENTS AND KITS CONTAINING THE SAME

This is a continuation-in-part of U.S. Ser. No. 241,608, filed Sep. 8, 1988, now abandoned. This application is also a continuation-in-part of U.S. Ser. No. 366,971, filed Jun. 14, 1989, which is a continuation-in-part of international application No. 07/003,226 (PCT/U.S. Ser. No. 87/03226), filed Nov. 12, 1987, which is a continuation-in-part of U.S. Ser. No. 061,937, filed Jun. 12, 1987, now abandoned, and U.S. Ser. No. 946,475, filed Dec. 24, 1986, now U.S. Pat. No. 4,803,170

TECHNICAL FIELD

This invention relates to phthalocyanine and tetrabenztriazaporphyrin reagents and their derivatives useful as fluorescent reporting groups, imaging agents, and also as therapeutic agents. The fluorescent reagents are useful in nucleic acid sequence analysis, nucleic acid probe and hybridization assays, fluorescence microscopy, flow cytometry, immunoassay, and fluorescence imaging. The reagents may also be useful as therapeutic agents in photodynamic applications.

BACKGROUND OF THE INVENTION

Fluorescent compounds (fluorophores) have been widely used in immunoassays, flow cytometry, fluorescence microscopy, and DNA sequencing. To date, the sensitivity of such assays has been limited by the spectral properties of available fluorophores.

In particular, automated DNA sequencing has become an important tool in molecular biology. The most successful strategies utilize the Sanger dideoxy chain termination method with either a 5'-fluorophore-labeled primer or fluorophore-labeled dideoxynucleotide triphosphates to generate a series of fragments. The resultant fragments are separated by electrophoresis. Careful selection of the enzyme, fluorophore, and reaction conditions has increased the size of DNA fragments that can be sequenced by such techniques from a hundred to nearly a thousand bases. For example, Applied Biosystems Incorporated (ABI) reports the ability to sequence nearly a 700 base pair stretch of DNA within 13 hours using a fluorophore-labeled primer. Despite advances in automated sequencing, the current technology does not allow single-run sequencing of kilobase and greater lengths of DNA. This limit is imposed, in part, by fluorophore detection and resolution. Signal detection could be improved by the use of fluorophores with more ideal spectral properties.

Recently, DNA sequencing systems have been described based on the use of a novel set of four chain-terminating nucleotides, each carrying a different chemically tuned succinylfluorescein dye distinguished by its fluorescent emission. Prober, J. M., et al., Science 238: 336–341, 1987; European Patent Application No. 87305848.1.

The effect of peripheral substitution of fluoro and cyano groups on the electronic properties of silicon dihydroxy phthalocyanine has been modelled. Hale, P. D. et al., J. Am. Chem. Soc. 109(20): 5943–5947, 1987. The calculated wavelength of absorbance for the parent silicon phthalocyanine was predicted to be 673 nm while the octacyano- and octafluoro-derivatives had calculated transitions at 685 and 756 nm, respectively. No mention of fluorescence is made in the report.

Introduction of phenoxy and thiophenoxy substituents into the phthalocyanine macrocycle reportedly led to an appreciable red shift in the long wavelength band in the visible absorbance spectra. Derkacheva, V. M., and E. A. Luk'yanets, J. Gen. Chem. USSR 50: 1874–1878, 1980. The sulfur substituted phthalocyanines were said to be more red-shifted in absorbance than the oxygen substituted derivatives and, in either case, the 3-substituted phthalocyanines were reportedly more greatly shifted than the 4-isomers. No fluorescence data was reported. Of the compounds discussed in the Luk'yanets report, only the metal free derivatives are potential fluorophores. The cobalt and copper analogs are nonfluorescent. Metal free phthalocyanines are not capable of being rendered reactive or water soluble by the techniques described herein since the metal free specie is unstable to some of these techniques, such as chlorsulfonation.

The application of aluminum phthalocyanines to simultaneous, multicomponent fluorescence analysis such as in nucleic acid sequence analysis, flow cytometry, immuno- or nucleic acid probe assays requires the preparation of a family of tetherable, water-soluble derivatives with a common excitation wavelength and yet different emission wavelengths, with maximal spectral resolution between each family member. For DNA sequence analysis, four such fluorophores are desired.

Ideal fluorophores have five characteristics: a readily accessible excitation wavelength with a large molar absorptivity, a high fluorescence quantum yield, a large Stokes shift (>50 nm), emission at long wavelengths (greater than 600 nm), and a sharp emission profile (full width at half maximum, FWHM <40 nm).

Aluminum phthalocyanine (AlPc) has nearly ideal spectral properties. Excitation of aluminum phthalocyanine at 350 nm results in emission at 685 nm with fluorescence quantum yield ($\phi_f$) of 0.58. Brannon, J. H., and D. Magde, J. Amer. Chem. Soc., 102(1): 62–65, 1980. Aluminum phthalocyanine (AlPc) is composed of a highly conjugated macrocycle and a trivalent aluminum atom. The structure of the parent AlPc fluorophore is shown below. L is a ligand such as OH when the AlPc is in water. The trivalent aluminum atom provides axial ligation which serves to reduce aggregation and thereby increases fluorescence in solution.

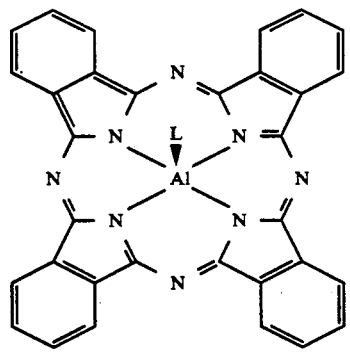

In a related application, U.S. Ser. No. 366,971, filed Jun. 14, 1989, the present inventors have disclosed water-soluble phthalocyanine compounds that are monomerically conjugated to biochemical moieties.

In therapeutic applications, aluminum phthalocyanine sulfonates have been determined to be effective in directed cell killing. Ben-Hur, E. and I. Rosenthal, Photochem. Photobiol. 42(2): 129-133, 1985. The advantage that phthalocyanines have over other photodynamic agents is their large molar absorptivity in the red region of the visible spectrum. The large molar extinction coefficient coupled with the transparency of tissue at these red wavelengths provides for more efficient light penetration and subsequently more effective treatment of subcutaneous malignancies. Pursuant to the present invention, aluminum phthalocyanine derivatives red-shifted from the parent compound will provide an even greater depth of penetration and enable even more effective treatments. Derivatives attached to biological moieties such as probes or antibodies can be targeted to specific cell populations.

Closely related to the phthalocyanines are the tetrabenztriazaporphyrins, referred to herein as TBTAPs. Barrett, P. A., et al., J. Chem. Soc. 1809–1828, 1937. The only structural difference is the replacement of the nitrogen at position twenty of the phthalocyanine with a substituted carbon. No substituted derivatives of these compounds have been reported to data. Nor have any tetherable or water soluble analogs been reported. The spectral and luminescent properties of magnesium and palladium benzoporphyrins have been reported. Solovev, K. N. et al., Opt. Spectrosc. 27: 24–29, 1969. Neither aluminum, substituted, tetherable or water-soluble derivatives are discussed.

SUMMARY OF THE INVENTION

One aspect of the present invention involves red-shifted, water-soluble phthalocyanine and tetrabenztriazaporphyrin (TBTAP) reagents having the formula:

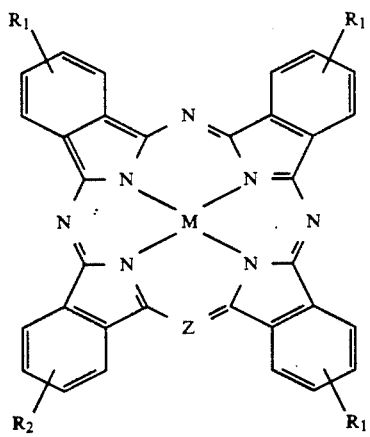

wherein M is $H_2$, aluminum, silicon, phosphorus, gallium, germanium, cadmium, scandium, magnesium, tin, or zinc. Each $R_1$ is independently selected from —XYW, —YW, —W, or —H. X is $CR_3R_4$, where $R_3$ and $R_4$ are independently selected from hydrogen, alkyl (preferably $C_1$–$C_{12}$), aryl (preferably $C_6$–$C_{12}$), or aralkyl (preferably $C_6$–$C_{12}$), or $R_3$ and $R_4$ together may be a carbonyl oxygen, or X is either phenyl or a heteroatom preferably selected from among oxygen, nitrogen, and sulfur. Y is a linking group between X and W or between a benzo ring of the phthalocyanine or TBTAP macrocycle and W. W is a water-soluble group. $R_2$ comprises a biological entity such as an antibody, antigen, nucleotide, nucleic acid, oligonucleotide, avidin, streptavidin, or a membrane probe, or $R_2$ is a reactive or activatable group suitable for conjugation to a biological entity. Z is N or C—R, where R is H or an organic group such as alkyl (preferably $C_1$–$C_{12}$), aryl (preferably $C_6$–$C_{12}$), or aralkyl (preferably $C_6$–$C_{12}$). When Z is CR, the $R_1$ and $R_2$ groups may be located on any of the four benzo rings of the TBTAP.

In a separate embodiment, the $R_2$ group located on the benzo ring in formula I is defined as $R_1$, and Z=—$CR_2$, where $R_2$ is the same as previously described. Thus, in this embodiment, the biological entity is located on the meso carbon atom of the macrocycle rather than on a benzo ring.

In all embodiments of formula I, the linking group Y is preferably less than 4 atoms in length and may contain aliphatic, aromatic, polyene, alkynyl, polyether, polyamide, peptide, amino acid, polyhydroxy, or sugar functionalities. Suitable water solubilizing groups W include —OH, —$CO_2H$, —$OCH_2CO_2H$, —$PO_4^=$, —$PO_3^-$, —$SO_3^-$, —$SO_2^-$, —$SO_2Cl$, —$SO_4^=$, —$NH_2$, —NHD, —$NHD_1D_2$, or —$N^+D_1D_2D_3$, D–$D_3$ being independently alkyl (preferably $C_1$–$C_{12}$), aryl (preferably $C_6$–$C_{12}$), or aralkyl (preferably $C_6$–$C_{12}$). Charged species will have counterions.

In a preferred embodiment, M is aluminum, each $R_1$ is —XYW, X is either an oxygen or sulfur atom, Y is a methylene group, W is a carboxylic acid, Z is nitrogen and $R_2$ is —X—$CH_2CO_2H$. The substitution of $R_1$ occurs at the 1,8,15,22 positions (3 isomer) or at the 2,9,16,23 positions (4 isomer) of the macrocycle. See FIG. 1 for the phthalocyanine and tetrabenztriazaporphyrin ring numbering system.

In a particularly preferred embodiment, M is aluminum, each $R_1$ is —XYW, X is either an oxygen or sulfur atom, Y is phenyl, W is sulfonate or sulfonyl chloride, Z is nitrogen and $R_2$ is —O-phenyl-sulfonate, —O-phenyl-sulfonyl chloride, —S-phenyl-sulfonate, or —S-phenyl-sulfonyl chloride. The substitution of $R_1$ occurs at the 1,8,15,22 positions (3 isomer) or at the 2,9,16,23 positions (4 isomer) of the macrocycle.

For the tetrabenztriazaporphyrin derivatives, the preferred embodiments are as described above except that Z is a carbon substituted with either hydrogen or phenyl substituents. The phenyl may be unsubstituted or substituted by 1–5, preferably 1–2 substituents selected from among $C_1$–$C_6$ alkyl, halogen (e.g. Cl, Br, F, I), carboxy, nitro, or other substituents that do not substantially interfere with the fluorescence or water solubility of the molecule.

When Z is —$CR_2$, the rest of the macrocycle contains 4 $R_1$ groups, as defined above.

For the divalent metals (M), Cd, Mg, and Zn, no axial ligand (L) is present. The trivalent metal atoms (M), Al, Ga, and Sc, have at least one axial ligand (L). The tetravalent metal atoms (M), Si, Ge, Sn, have at least two axial ligands (L). Phosphorus (M) will bear either one or three axial ligands (L).

Reagent kits for detection of single analytes using a reagent described above are provided, as are kits and methods for sequencing DNA. Reagent kits useful for simultaneous detection of a plurality of analytes in solution containing combinations of the subject reagents, each tethered to a different biological entity, are also disclosed.

A second aspect of the present invention involves pyrazine porphyrazines, pyrazine tetrabenztriazaporphyrins, pyridine porphyrazines, and pyridine tetrabenztriazaporphyrins. These compounds have the same structure as formula I, with the exception that 1–4 of the benzo rings contain 1 nitrogen atom (pyridine derivatives) or 2 nitrogen atoms (pyrazine derivatives). When the benzo ring contains 1 nitrogen atom, both the 3 and 4 positional isomers are possible. The 2 nitrogen atoms per ring in the pyrazine derivatives are generally oriented in a 1,4 arrangement in the benzo ring. Preferably, all 4 benzo rings will contain either 1 or 2 nitrogen atoms. Mixed derivatives are also possible, in which 1-3 benzo rings contain one nitrogen atom (either isomer) and 3-1 benzo rings contain 2 nitrogen atoms. The $R_1$ and $R_2$ groups may be attached to carbon atoms or nitrogen atoms in the benzo rings, but attachment to carbon atoms of the benzo rings is preferred. When X is a heteroatom, —XYW will be attached to a carbon; when X is $CR_3R_4$ or phenyl, —XYW may be attached to a carbon atom (preferred) or a nitrogen atom of the benzo ring. Examples 12 and 13 herein illustrate preferred compounds of the second aspect compounds. Additional preferred compounds are analogous to those identified for the compounds of the first aspect of the present invention. The compounds of the second aspect of this invention may be used in the same applications as the phthalocyanine and tetrabenztriazaporphyrin compounds described above.

A third aspect of the present invention involves cationic reagents having formula I above, except that $R_2$ is $R_1$. $R_1$, X and Y are as described above. W is —$N^+D_1D_2D_3$, wherein $D_1$–$D_3$ are independently hydrogen, $C_1$–$C_{12}$ alkyl, $C_6$–$C_{12}$ aralkyl, or $C_6$–$C_{12}$ aryl groups, or —$N^+D_1D_2D_3$ forms a pyridinium ring. The charged groups may be associated with any conventional counterion as long as it does not substantially interfere with fluorescence or synthesis of the reagent. These reagents may be advantageously used to bind to (stain or label) oligo- and polynucleotides, especially DNA or RNA, for qualitative or quantitative determination.

In yet another aspect, the present invention provides intermediates for the synthesis of the compounds of formula I. For example, reactive or activatable intermediates in which $R_2$ in formula I is a group capable of being covalently attached to a biological entity are contemplated. $R_2$ may be directly attached to the benzo ring or may be linked to the benzo ring by an XY or Y linkage. Such $R_2$ groups include —$SO_2Cl$; —$CO_2H$; —COX', wherein X' is a leaving group such as N-hydroxy-succinimide; maleimide; or isothiocyanate. $R_2$ can also be a nucleophilic moiety, such as an amino group, for reaction with reactive groups on the biological entity. A water soluble group W on the benzo rings may alternatively be conjugated to biological entities, in some embodiments. The other variables in formula I are the same as defined herein. These compounds may be coupled to biological entities by standard coupling reactions. Once coupled, at least a portion of the reactive group becomes a Y' group, as defined in connection with formula I.

DETAILED DESCRIPTION OF THE PREFERRED EMBODIMENTS

Figure 1:
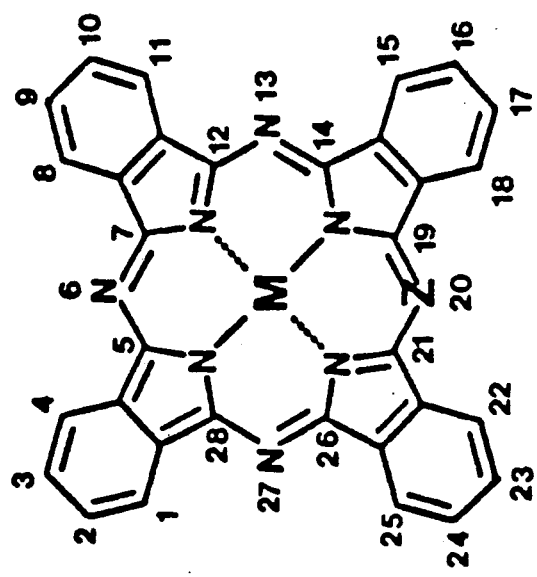
FIG. 1 shows the phthalocyanine and tetrabenztriazaporphyrin ring numbering system.
Figure 2:
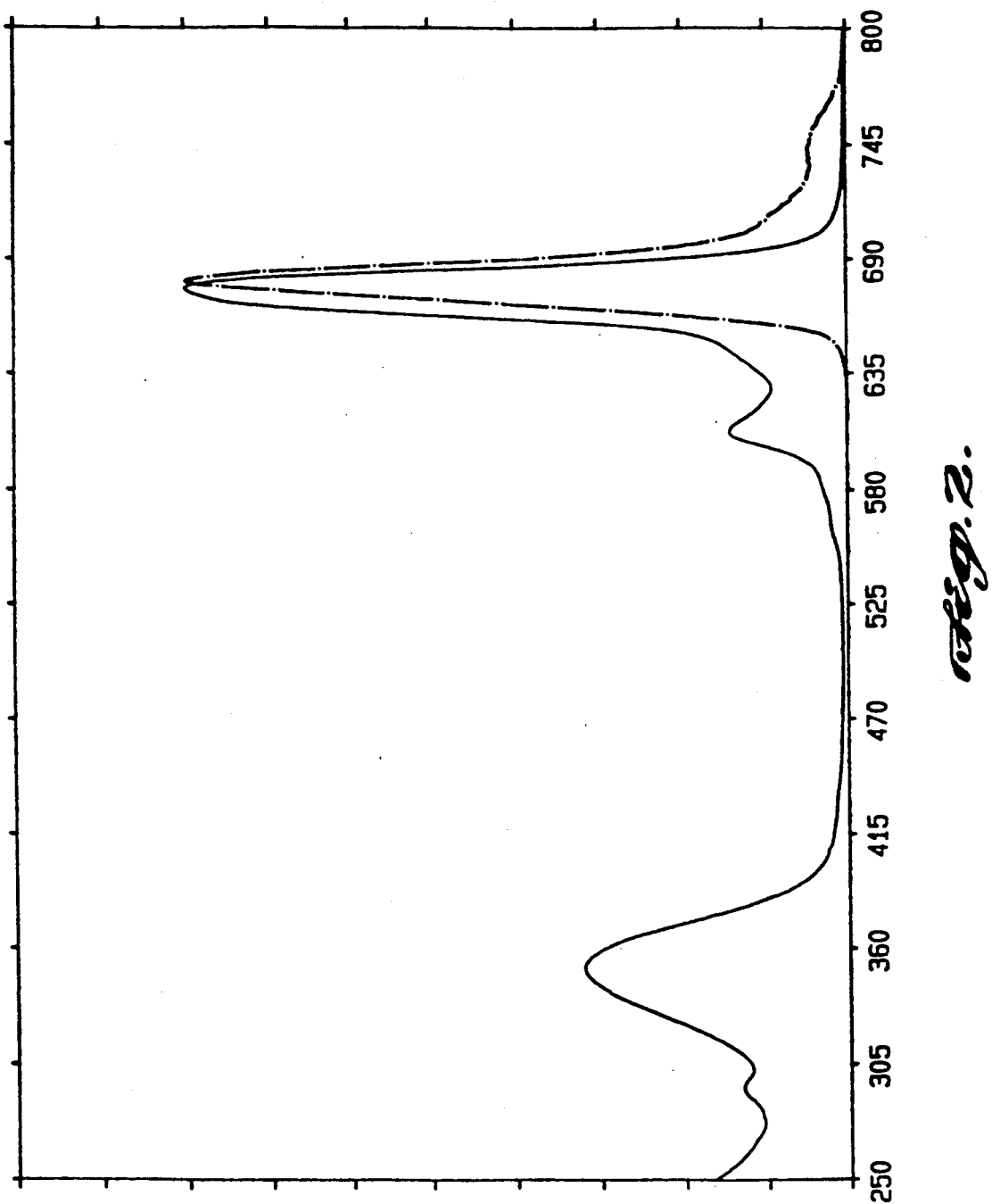
FIG. 2 shows the absorbance and emission spectrum of aluminum phthalocyanine tetrasulfonate, 1, in water.

The invention, in a first aspect, provides improved phthalocyanine and related reagents in the form of red-shifted, water-soluble, monomerically-tetherable derivatives according to formula I.

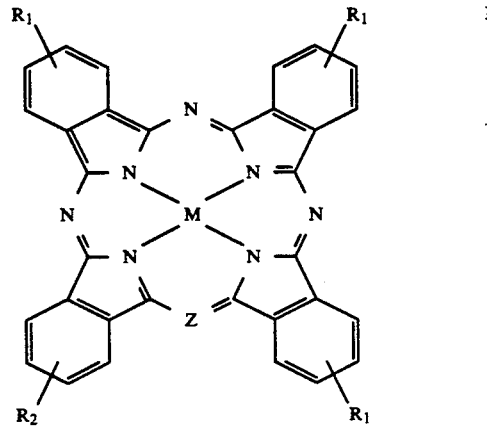

In formula I, M represents either $H_2$ or is selected from among the following metals: aluminum, silicon, phosphorous, gallium, germanium, cadmium, scandium, magnesium, tin, and zinc. Each $R_1$ is independently selected from —XYW, —YW, —W, or hydrogen. X represents $CR_3R_4$, where $R_3$ and $R_4$ are independently selected from hydrogen, alkyl (preferably $C_1$-$C_{12}$), aryl (preferably $C_6$-$C_{12}$), or aralkyl (preferably $C_6$-$C_{12}$), or $R_3$ and $R_4$ together may be a carbonyl oxygen, or X is phenyl, or X is a heteroatom selected from among oxygen, nitrogen, sulfur, phosphorus, silicon, and selenium. Y represents a linking group; and W represents a water solubilizing group. The substituent $R_2$ is selected from among —A, —Y'A, —XA, and —XY'A, where A denotes a biological entity such as an antibody, antibody fragment, antigen, oligonucleotide, nucleotide, nucleic acid probe, avidin, streptavidin, or membrane probe. $R_2$ may also be a reactive or activatable group which is directly attached to the benzo ring or attached by way of a linker, such as —X-alkylene— or —X-phenylene—, where X is defined above. Z is N or C—R, where R is H, or an organic group such as alkyl (preferably $C_1$-$C_{12}$), aryl (preferably $C_6$-$C_{12}$), or aralkyl (preferably $C_6$-$C_{12}$). Y' is a linking group that tethers the biological entity (A) to the phthalocyanine or tetrabenztriazaporphyrin macrocycle. The biological entities containing nucleotides or derivatives thereof are generally triphosphorylated, but mono- and di-phosphorylated compounds may also be employed. Z is either a nitrogen atom or a carbon substituted with hydrogen, alkyl (preferably $C_1$-$C_{12}$), aryl (preferably $C_6$-$C_{12}$), or aralkyl (preferably, $C_6$-$C_{12}$) groups.

In a separate embodiment, Z is —$CR_2$, in which case all of the variables on the benzo rings of the macrocycle will be $R_1$ groups; that is, the $R_2$ group may be attached to the meso carbon rather than to a benzo ring of the TBTAPs.

In a preferred embodiment, M is aluminum, each $R_1$ is —XYW, X is either oxygen or sulfur, Y is methylene, W is carboxylate, Z is nitrogen, and $R_2$ is an activatable or reactive group attached to the benzo ring by way of an XY link. $R_2$ may preferably be —XY-activatable group, where X is O, Y is methylene and the activatable group is —$CO_2H$.

In a particularly preferred embodiment, M is aluminum, each $R_1$ is —XYW, X is either oxygen or sulfur, Y is phenyl, W is sulfonate or sulfonyl chloride, $R_2$ is an activatable or reactive group attached to the benzo ring by way of an XY link, and Z is nitrogen. These derivatives are referred to as tetrasubstituted aluminum phthalocyanines. $R_2$ may preferably be —XY-reactive group, where X is O or S, Y is phenyl and the reactive group is —$SO_2Cl$ (located in the ortho, meta, or para positions of the phenyl ring).

A similar preferred embodiment is exactly as above except that Z is a carbon with either a hydrogen or phenyl substituent. These derivatives are referred to as tetrasubstituted tetrabenztriazaporphyrins.

Based on the synthetic procedures used, some of the present compounds may occur as mixtures, particularly isomeric mixtures or mixtures of compounds with different numbers of water solubilizing groups. Such mixtures are within the scope of this invention.

While the phthalocyanines all share a common absorbance wavelength in the ultraviolet near 350 nm, the visible absorbance is substituent dependent. A red shift of the visible absorbance maxima of phthalocyanines is attained by peripheral substitution with oxygen (ether) and sulfur (thioether) groups, X in formula I. Sulfur substitution results in a greater red shift of fluorescent emission than oxygen substitution, and substitution at the three positions (1,8,15,22 isomer) provides a greater shift than 4 substitution (2,9,16,23 isomer). The trend observed in the absorbance spectra is found in the fluorescence spectra. The trend is also observed in the absorbance and emission maxima of tetrabenztriazaporphyrins. In view of these observations, a preferred group of reagents are those in which at least one X is a heteroatom, although 2, 3 or 4 heteroatoms are also contemplated.

Substituent W is provided to impart water solubility to the reagent, preferably at $10^{-6}$M or lower concentrations. The aqueous solubility should be maintained at temperatures ranging from about 4° C. (e.g., for flow cytometric applications) to about 100° C. (e.g., 67° C. for gene probe applications). Additionally, W is chosen to provide maximum monomerism or, in other words, to minimize aggregation of the fluorophores in aqueous solution. Aggregation of the fluorophores results in the quenching of fluorescence and thus limits the sensitivity of the probe and therefore its utility in assay environments. Monomerism is discussed in greater detail hereinbelow. Since charge repulsion diminishes aggregation, W is preferably charged rather than neutral. However, W must not promote nonspecific binding. Thus, for nucleic acid sequencing, the W groups should be negatively charged (W is sulfonate, for example) in order to avoid ionic attraction to negatively charged DNA or RNA. Conversely, a positively charged phthalocyanine derivative (W is quaternary ammonium, for example) may be utilized to selectively stain DNA, RNA, and other negatively charged cellular constituents.

Guided by the foregoing considerations, the water solubizing groups W can be selected from among —OH, —poly-OH, —$CO_2H$, —$OCH_2CO_2H$, —$OCHD_1CO_2H$, —$OCD_1D_2CO_2H$, —$PO_4^{2-}$, —$PO_3^-$, —$SO_3^-$, —$SO_2^-$, —$SO_4^{2-}$, —$SO_2Cl$, —$N^+H_3$/—$NH_2$, —$N^+H_2D$/—NHD, —$N^+HD_1D_2$/—$ND_1D_2$, and —$N^+D_1D_2D_3$ with D-$D_3$ being individually alkyl (preferably $C_1$-$C_{12}$), aryl (preferably $C_6$-$C_{12}$), or aralkyl (preferably $C_6$-$C_{12}$), amino acids (such as one selected from the common 20 naturally occurring amino acids) or peptides (e.g. having from 2-10 residues). In particular, sulfonate groups (preferably 2, 3 or 4) render the molecule water soluble over a wide range of pH (2-12). Carboxylic acid groups, on the other hand, are more sensitive to pH, thus limiting their versatility and performance in aqueous systems. Below pH 5, carboxylic acid groups are not ionized and therefore have limited solubility in water. Both sulfonic and phosphoric acids are ionized below pH 2. Quaternary ammonium groups are positively charged regardless of pH. Charged groups will be associated with a suitable counterion. The counterions are not necessarily limited and may be any known counterions that do not interfere with synthesis of the compounds or their desirable fluorescence characteristics.

Substituent Y is a group of atoms that links X with the water solubilizing group W or the reactive or activatable group $R_2$. In a preferred embodiment Y is methylene (—$CH_2$—); however, longer alkyl, aryl, or aralkyl chains are possible (preferably $C_2$-$C_{12}$). Longer links may adversely impact water solubility and increase aggregation in solution leading to a diminution of fluorescence. Therefore, in a preferred embodiment Y has about 7 carbon atoms or less. Alternatively, the link Y may be hydrophilic or even charged to increase both water solubility and monomerism. Suitable hydrophilic spacers include polyethers, polyamines, polyalcohols, and naturally occurring sugars, peptides, and nucleotides. In a particularly preferred embodiment, Y is phenyl with X at position one and W at position 4 (para substitution).

Within the above constraints, Y can be selected from among aliphatic, aromatic, mixed aliphatic/aromatic functionalities, polyene (cis or trans), mixed polyene and/or aliphatic and/or aromatic functionalities, alkynyl, mixed alkynyl and/or aliphatic and/or aromatic functionalities, polyether linked by aliphatic and/or aromatic and/or alkenyl and/or alkynyl functionalities, polyamides, peptides, amino acids, polyhydroxy functionalities, sugars, and nucleotides. The precise nature of Y is unimportant, and practically any Y group will work as long as it does not interfere with water-solubility or fluorescence to an unacceptable degree and it is synthetically accessible.

Substituents $R_1$ are individually selected from among —XYW, —YW, —W, and hydrogen. In one preferred embodiment, all three $R_1$ groups are —XYW, —YW, or —W, especially —XYW. In another preferred embodiment, one $R_1$ is —XYW and the other two are —YW or —W.

Substituent $R_2$ may be a biological entity such as an antigen or an antibody attached to the macrocycle. $R_2$ may also be an activatable group or a reactive group; as such, $R_2$ may be linked to the benzo ring by X or XY linkers, or may be directly attached to the benzo ring. In some embodiments, discussed herein, $R_2$ may be $R_1$, in which case no biological entity is covalently bound to the fluorophore. In other embodiments, $R_2$ is attached to the meso carbon of a TBTAP or other derivatives of a triazaporphyrin described herein, and the remaining variables on the benzo rings of the macrocycle are each $R_1$. Representative biological entities (A) include natural or synthetic drugs (therapeutics and abused), drug metabolites, metabolites, hormones, peptides, nucleotides (e.g., ATP, CTP, GTP, TTP, UTP, dATP, dGTP, dCTP, dTTP, dUTP, ddATP, ddCTP, ddGTP, ddTTP, ddUTP, and derivatives thereof), neurotransmitters, enzyme substrates, DNA or RNA probes, DNA or RNA (oligo and polynucleotides), DNA/RNA hybrids, DNA/DNA hybrids, RNA/RNA hybrids, growth factors, antibody fragments (antigen binding fragments), antibodies (polyclonal or monoclonal), serum proteins, streptavidin, avidin, enzymes, intracellular organelles, cell surface antigens, receptors, ligand binding proteins or associated ligands, membrane probes etc. The fluorescent moiety (i.e., the macrocycle) is preferably attached to $R_2$ monomerically to enhance fluorescence. The particular nature of the biological entity is relatively unimportant. As long as the conjugation of the fluorophore to the biological entity does not destroy utility of the conjugate, it is contemplated to be within the scope of this invention.

By "membrane probe" is meant a lipophilic organic moiety preferably having 10 to 30 carbon atoms. In a preferred embodiment, the membrance probe is a long chain hydrocarbon group. Particularly preferably, the hydrocarbon group is a saturated $C_{10}$-$C_{30}$ alkyl group that may be straight chain, branched or may contain cyclic rings. The membrane probe may be attached to a benzo ring or to the meso carbon of a TBTAP.

Preferred linkers Y' for connecting the biological entity to the phthalocyanine include sulfonamide, amide, ether, thioether, ester, thioester, amine, and carbon-carbon bonds. For this purpose, the biological entity should bear a terminal amino, carboxy, $\alpha$, $\beta$-unsaturated carbonyl, thiol, sulfonyl chloride, or halide group for attachment to the phthalocyanine. In turn, the phthalocyanine should bear a correspondingly reactive group, such as carboxy, amino, thiol, $\alpha,\beta$-unsaturated carbonyl, sulfonyl chloride, or hydroxy.

The tether Y' to the biological entity, A, in $R_2$ is long enough for optimal recognition of A in typical biological assays. Displacement of A from the phthalocyanine or tetrabenztriazaporphyrin can be further enhanced by the use of a rigid linker containing for example, alkene, acetylene, cyclic, aromatic or amide groups. The water solubility of the phthalocyanine may also be enhanced by selection of hydrophilic or charged groups as part of the linker Y'. Hydrophilic spacers include polyethers, polyamines, polyalcohols, and naturally occurring species such as sugars, peptides, and nucleotides. To reduce aggregation in aqueous solution long, hydrophobic tethers should be avoided.

The following are illustrative embodiments of some compounds of formula I of the present invention.

ALUMINUM PHTHALOCYANINE TETRAGLYCOLATES

In one embodiment, the invention provides companion water soluble aluminum phthalocyanine derivatives. In a preferred embodiment, the invention provides two aluminum tetraglycolylphthalocyanine isomers, 2 and 3, each having emission bands red-shifted relative to aluminum phthalocyanine trisulfonate (referred to as compound 1 herein). The tetracarboxylic acid derivatives may be prepared as set forth in Example 1 herein. The only difference between the two phthalocyanines is the position of attachment of the glycolyl group (—OCH$_2$CO$_2$H) on the macrocycle. Substitution at the 2,9,16,23 positions provides 2, while 1,8,15,22 substitution gives 3. The carboxylic acid groups present in these derivatives provides both water solubility and a reactive functionality for tethering compounds to biological entities. Exemplary biological entities for coupling to 2 and 3 are: antigens, antibodies or antibody fragments, receptors, intracellular organelles, proteins, such as avidin and streptavidin, enzyme substrates, membrane probes, nucleotides and derivatives thereof, nucleic acid probes, and nucleic acids.

Figure 3:
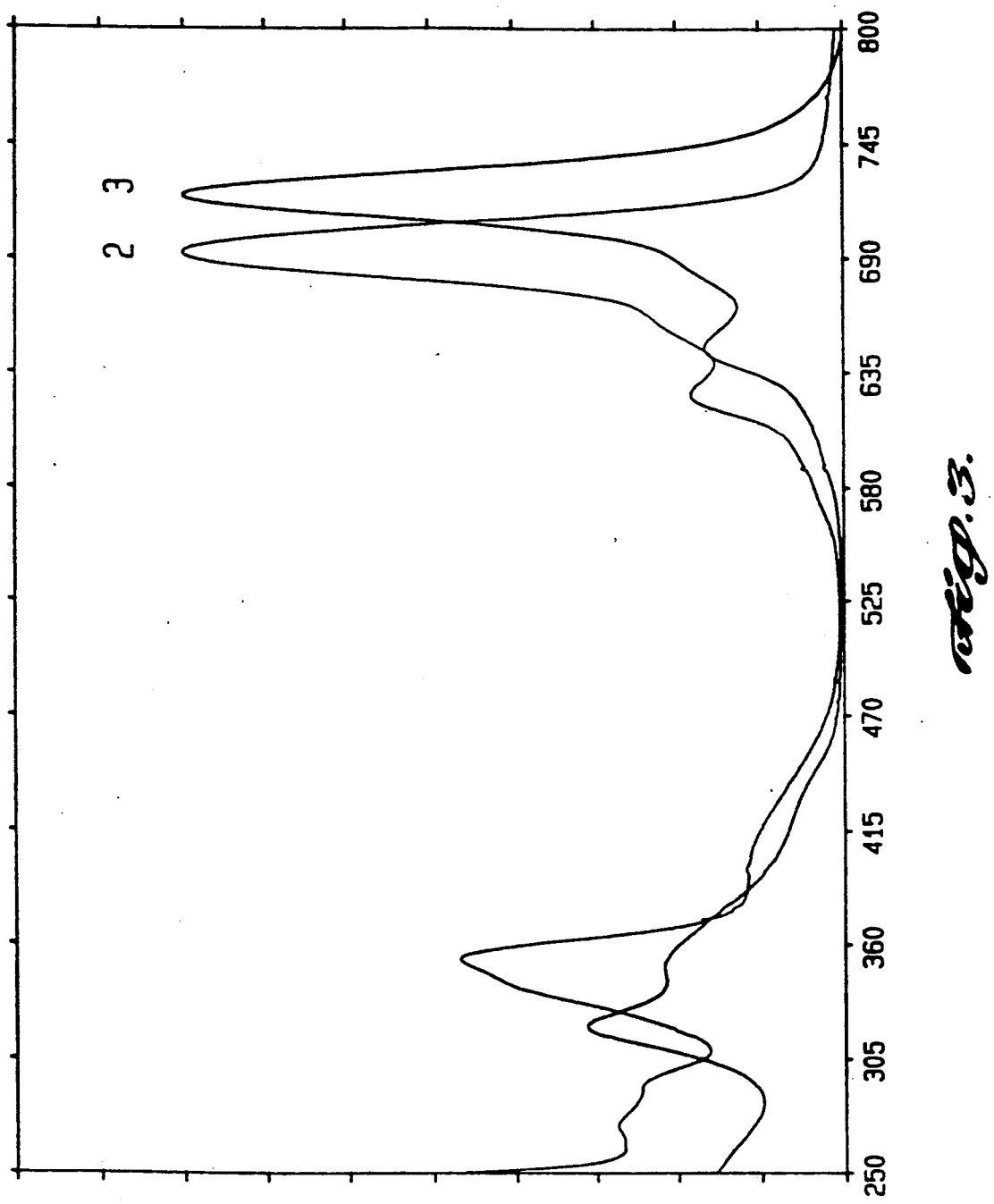
FIG. 3 compares the absorbance spectra of the glycolic acid derivatives, 2 and 3, in water.
Figure 4:
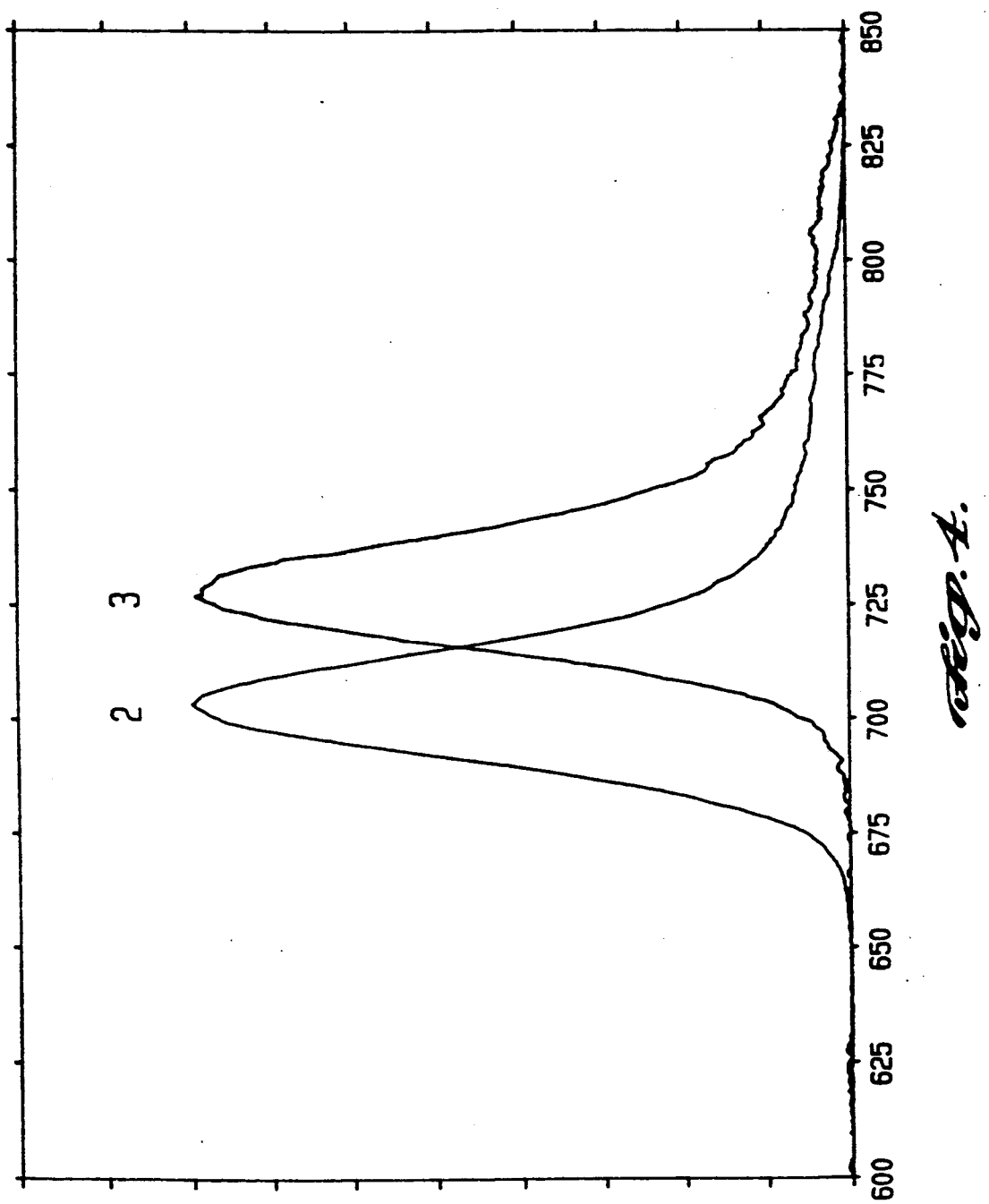
FIG. 4 compares the emission spectra of the glycolic acid derivatives, 2 and 3, in water.

The absorbance spectra of 2 and 3 in water are shown in FIG. 3. Both exhibit a common excitation wavelength in the ultraviolet (350 nm) with molar absorptivities around 70,000. As shown in FIG. 4, the emission maxima for the pair are distinguishable, with emission wavelengths of 704 nm for 2 and 727 nm and 3. The quantum yields of fluorescence are 0.55 and 0.43, for 2 and 3 respectively.

Figure 5:
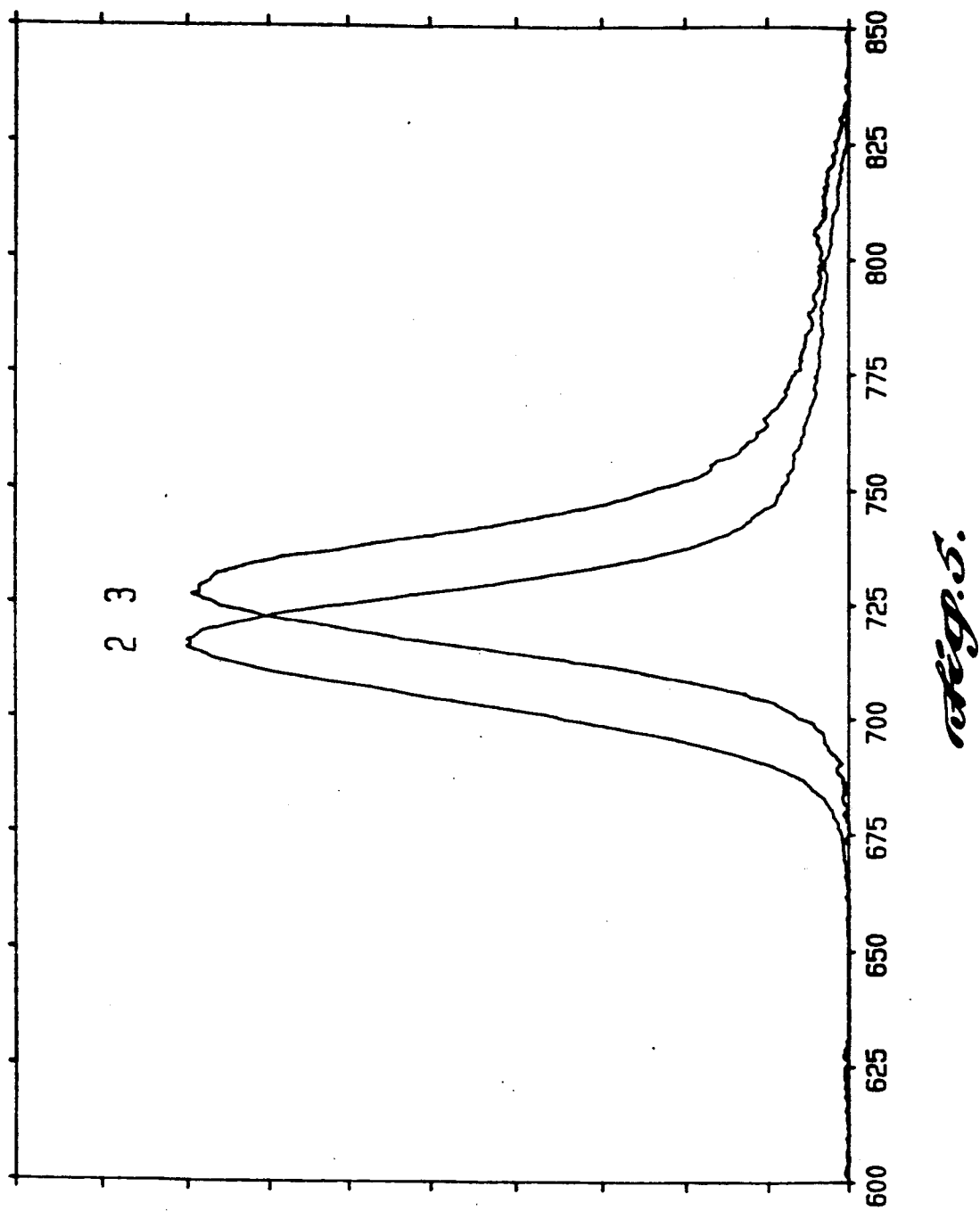
FIG. 5 compares the emission of spectra of the two glycolic acid derivatives, 2 and 3, in aqueous cetyl trimethylammonium bromide (CTAB).

The spectral resolution of the two fluorophores may be affected by environmental effects. FIG. 5 presents the emission spectra of 2 and 3 in aqueous cetyl trimethylammonium bromide (0.010M CTAB). While the emission maximum of 3 remains essentially unchanged, a dramatic red shift to 716 nm occurs for 2.

OXYGEN AND SULFUR SUBSTITUTED ALUMINUM PHTHALOCYANINE SULFONATES

In a most preferred embodiment, the invention provides a family of four novel, water soluble, tetherable aluminum phthalocyanine based fluorophores. The family consists of two pairs of isomeric aluminum phthalocyanine derivatives. The emission of each fluorophore pair is unique and distinguishable from the other and all are red-shifted compared to 1.

Figure 6:
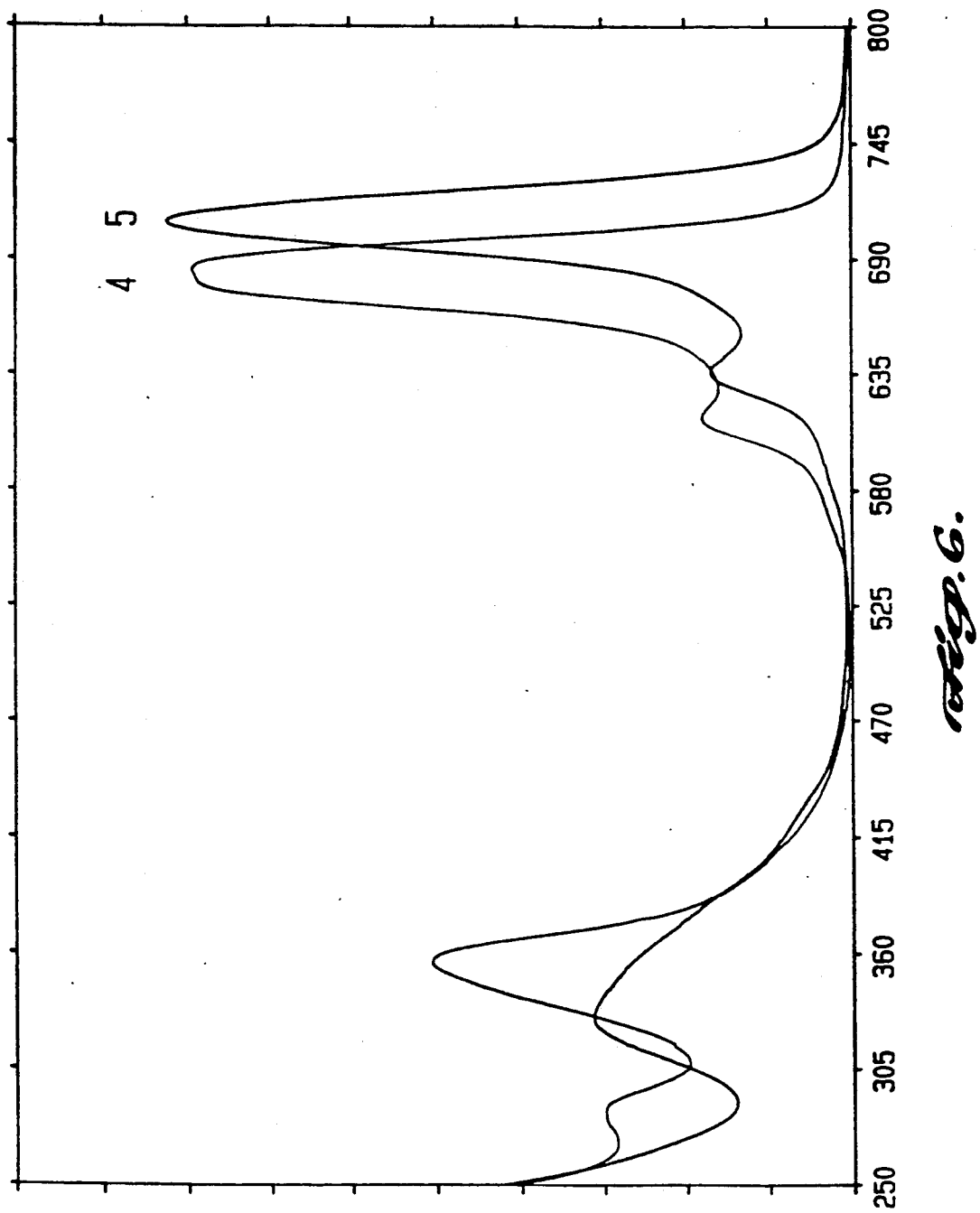
FIG. 6 compares the absorbance spectra of the oxygen substituted aluminum phthalocyanine sulfonates, 4 and 5, in water.
Figure 7:
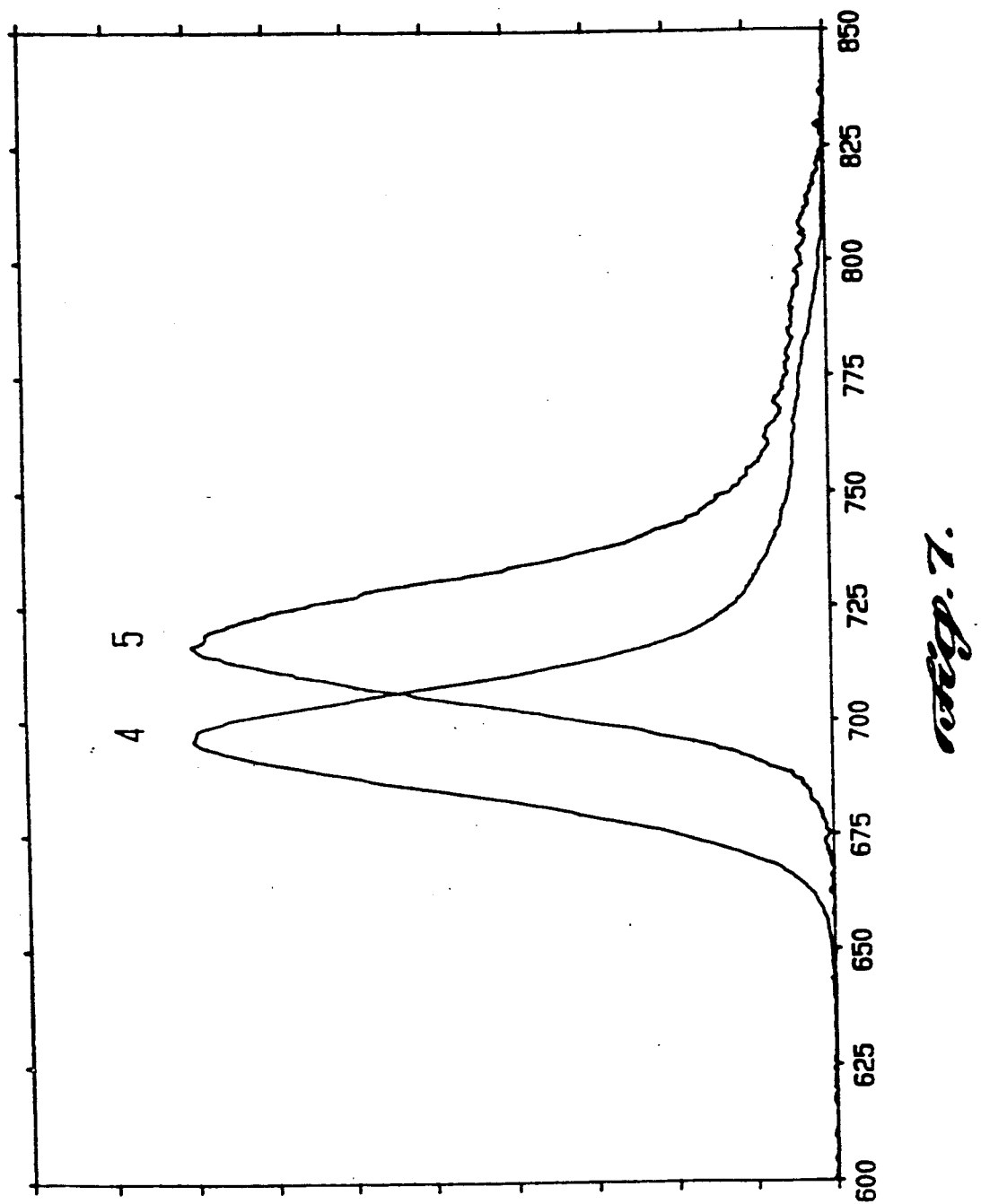
FIG. 7 compares the emission spectra of the oxygen substituted aluminum phthalocyanine sulfonates, 4 and 5, in water.

The first pair of fluorophores are tetraphenoxy substituted aluminum phthalocyanines. Phthalocyanine formation from 4-phenoxyphthalonitrile yields a 2,9,16,23 phenoxy substituted phthalocyanine. Similar reaction with 3-phenoxyphthalonitrile results in the formation of a 1,8,15,22 substituted phthalocyanine. After the incorporation of aluminum, treatment of these derivatives with chlorosulfonic acid produces reactive sulfonyl chloride derivatives which may be coupled to biological entities, such as antigens, antibodies or antibody fragments, receptors, intracellular organelles, proteins such as avidin and streptavidin, enzyme substrates, membrane probes, nucleotides and derivatives thereof, nucleic acid probes, and nucleic acids. The hydrolysis of the sulfonyl chloride to the sulfonic acid provides the water soluble analogs. The absorbance spectra of the sulfonated tetraphenoxy aluminum phthalocyanines, 4 and 5, in water are shown in FIG. 6. The emission spectra are shown in FIG. 7. The syntheses of 4 and 5 and a tabulation of their spectral properties are given in Example 2.

Figure 8:
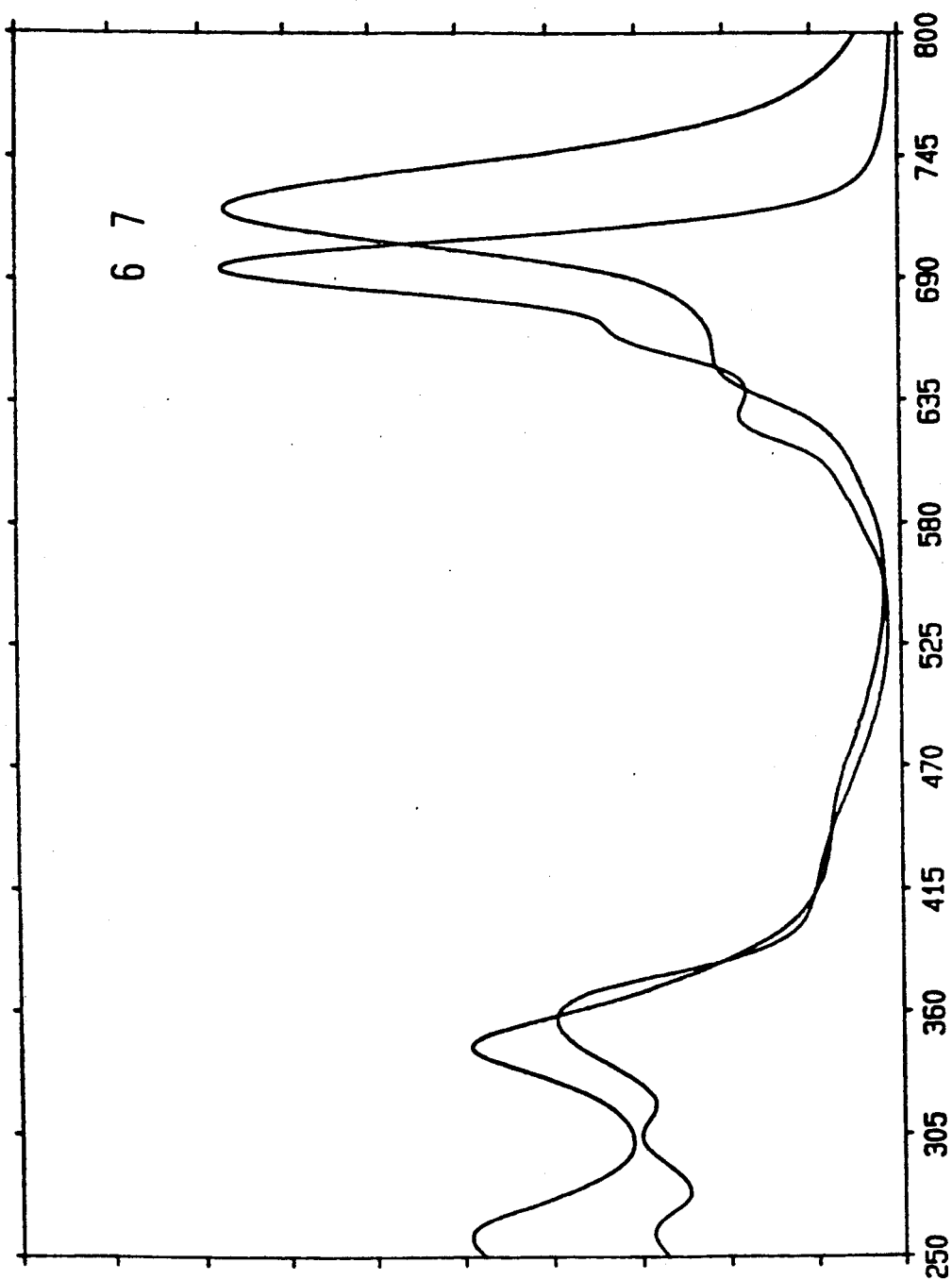
FIG. 8 compares the absorbance spectra of the sulfur substituted aluminum phthalocyanine sulfonates, 6 and 7, in water.
Figure 9:
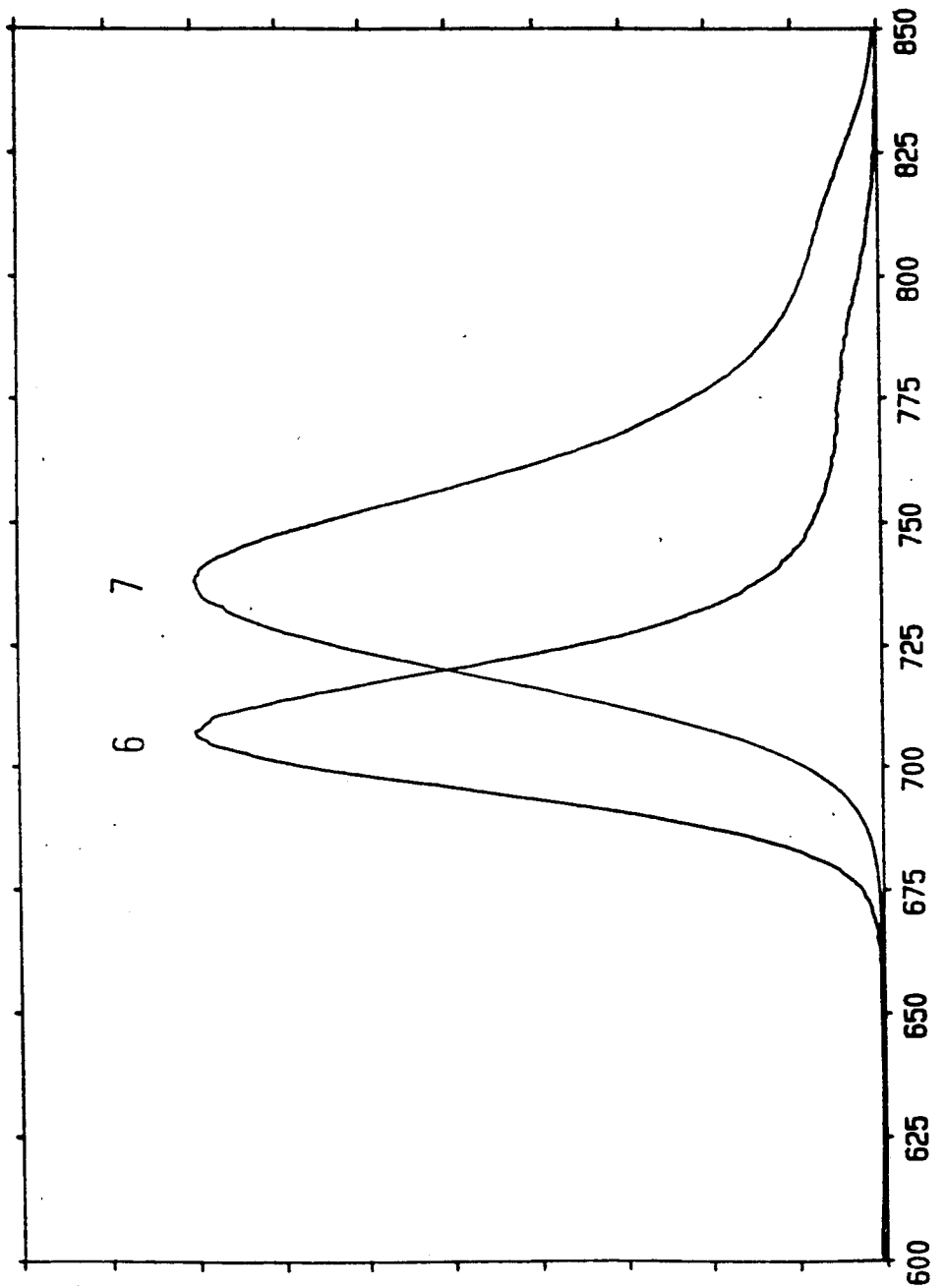
FIG. 9 compares the emission spectra of the sulfur substituted aluminum phthalocyanine sulfonates, 6 and 7, in water.

The second pair of fluorophores are tetrathiophenoxy substituted aluminum phthalocyanines. As above 4-thiophenoxyphthalonitrile provides the 2,9,16,23 substituted phthalocyanine, while 3-thiophenoxyphthalonitrile gives the 1,8,15,22 substituted isomer. After the incorporation of aluminum, treatment of these derivatives with chlorosulfonic acid yields a reactive form useful in coupling to biological entities. Hydrolysis produces sulfonates that are highly water soluble. The absorbance spectra of the sulfonated tetrathiophenoxy aluminum phthalocyanines, 6 and 7, in water are shown in FIG. 8. The emission spectra are presented in FIG. 9. The syntheses of 6 and 7 and a tabulation of their spectral properties are given in Example 2. These compounds may be attached to the above-mentioned reactive or activatable $R_2$ groups to yield conjugates that may be used for a variety of purposes, including sequencing of DNA.

OXYGEN AND SULFUR SUBSTITUTED ALUMINUM TETRABENZTRIAZAPORPHYRIN SULFONATES

In an alternative preferred embodiment, a second family of four novel fluorophores derived from the tetrabenztriazaporphyrin (TBTAP) system is presented. These fluorophores differ from phthalocyanines 4–7 above only in position 20 of the ring system. For the phthalocyanines, position 20 is a nitrogen atom, while for the tetrabenztriazaporphyrins, position 20 is a substituted carbon (in formula I, Z is N for phthalocyanines, Z is CR for the tetrabenztriazaporphyrins). In this embodiment, the 20 carbon is phenyl substituted.

As in the most preferred embodiment, the family of four aluminum TBTAP fluorophores consists of two pairs of oxygen and sulfur positional isomers. Reaction of benzylmagnesium bromide with each of the four phthalonitriles, 4-phenoxyphthalonitrile, 3-phenoxyphthalonitrile, 4-thiophenoxyphthalonitrile, and 3-thiophenoxyphthalonitrile provides TBTAP ring systems which are metalated with aluminum and sulfonated to provide compounds 8–11, respectively. The preparation of the aluminum 20-phenyl tetrabenztriazaporphyrins and the tabulation of their spectral properties are given in Example 3.

Figure 10:
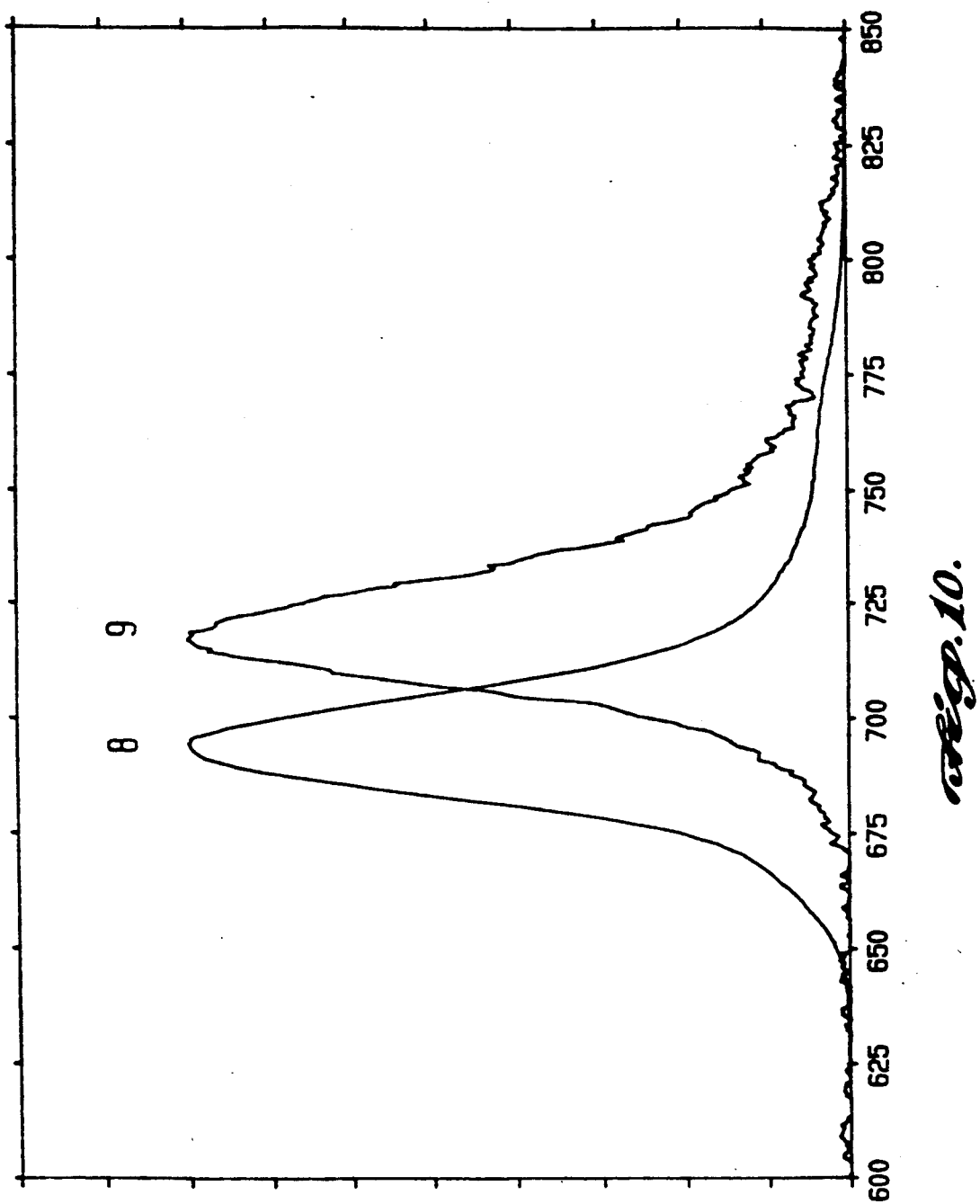
FIG. 10 compares the emission spectra of the oxygen substituted aluminum tetrabenztriazaporphyrin sulfonates, 8 and 9, in water.
Figure 11:
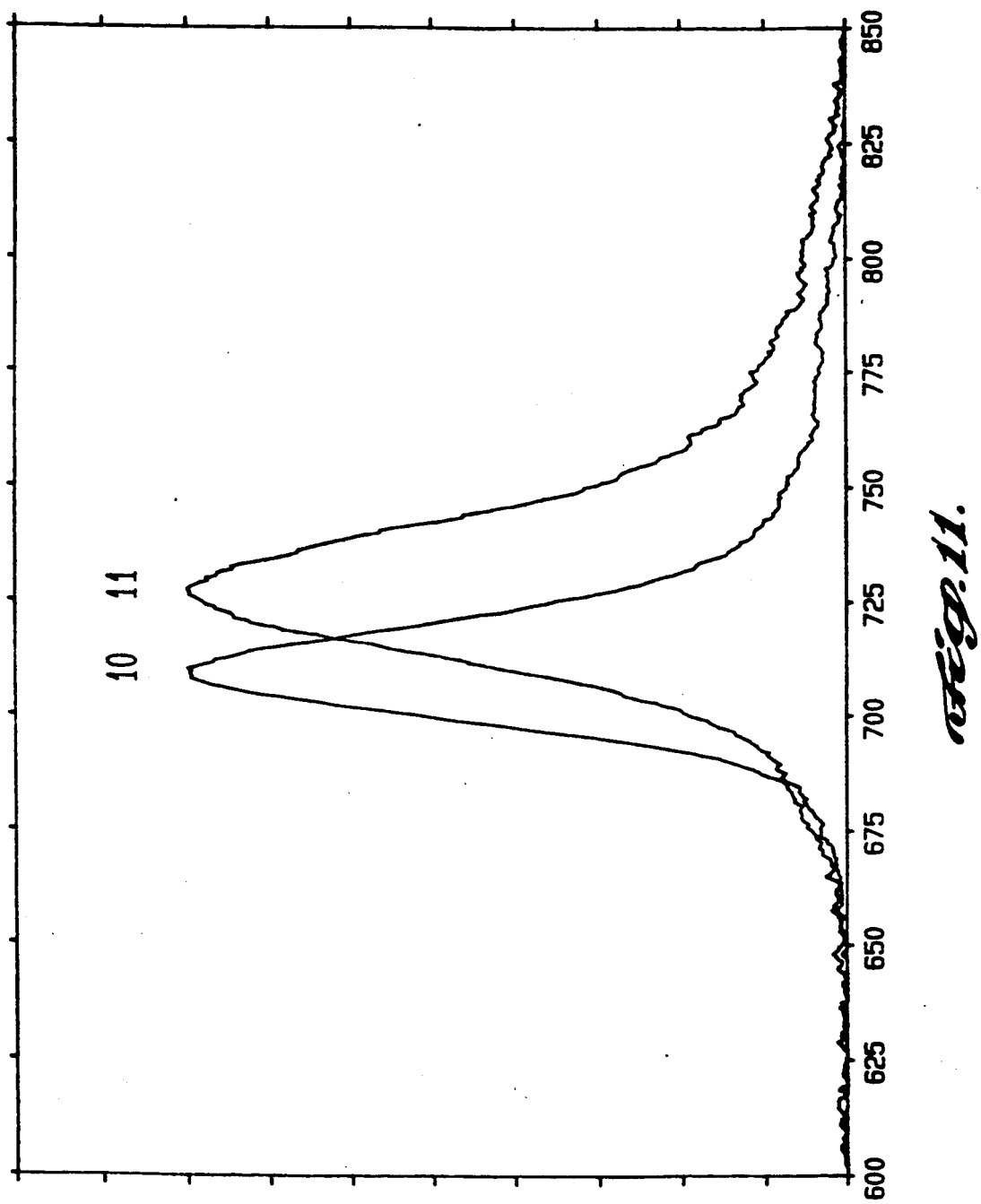
FIG. 11 compares the emission spectra of the sulfur substituted aluminum tetrabenztriazaporphyrin sulfonates, 10 and 11, in water.

The emission spectra of the aluminum tetraphenoxy TBTAP derivatives are shown in FIG. 10. Similarly, emission spectra of the tetrathiophenyl derivatives are shown in FIG. 11. As with the aluminum phthalocyanines, the TBTAP sulfur analogs are red-shifted relative to the oxygen counterparts, and the 1,8,15,22 isomers are red-shifted compared to the 2,9,6,23 isomers.

ALUMINUM TETRABENZTRIAZAPORPHYRIN SULFONATES

Figure 12:
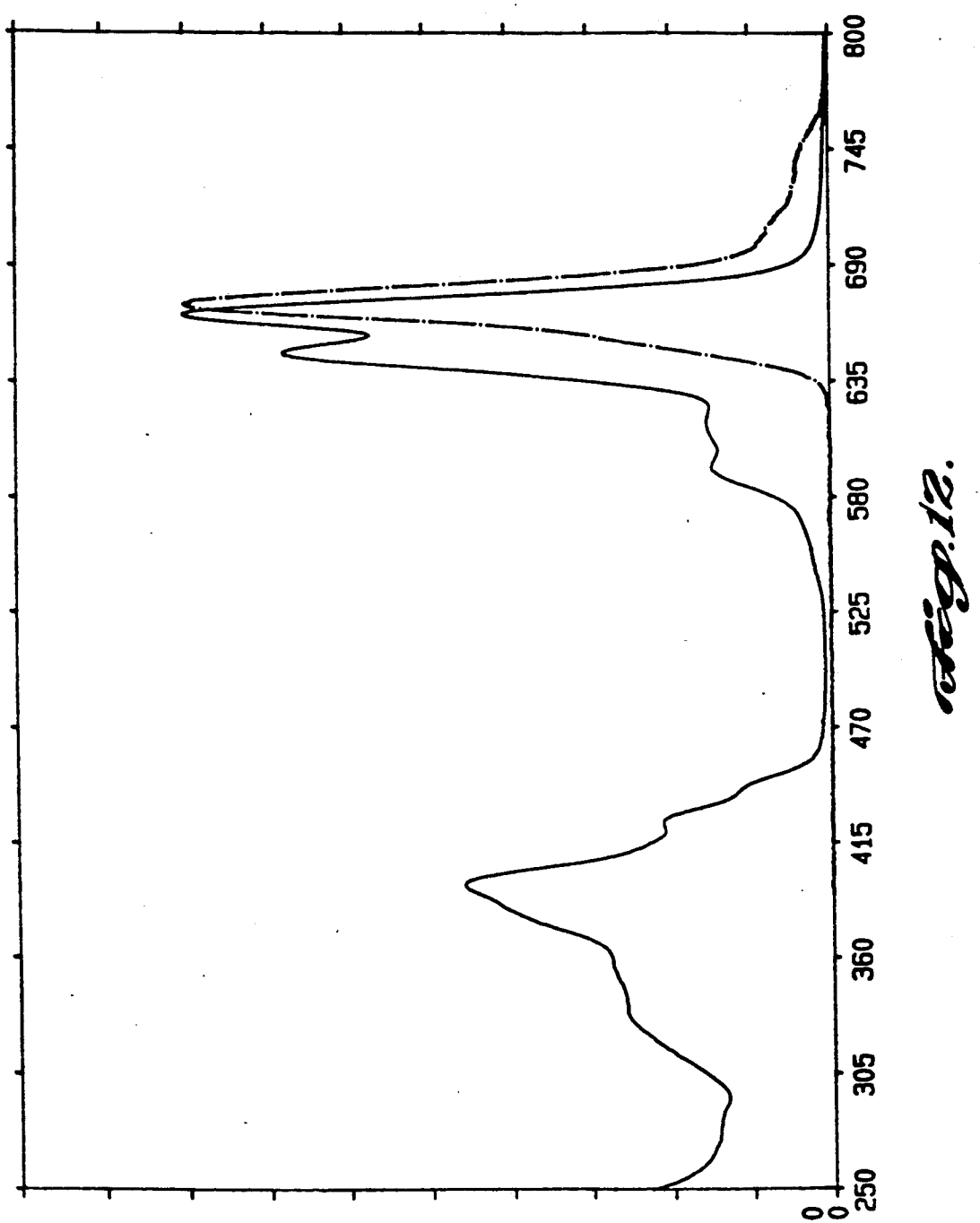
FIG. 12 shows the absorbance and emission spectra of aluminum 20-H tetrabenztriazaporphyrin sulfonate, 12, in water.
Figure 13:
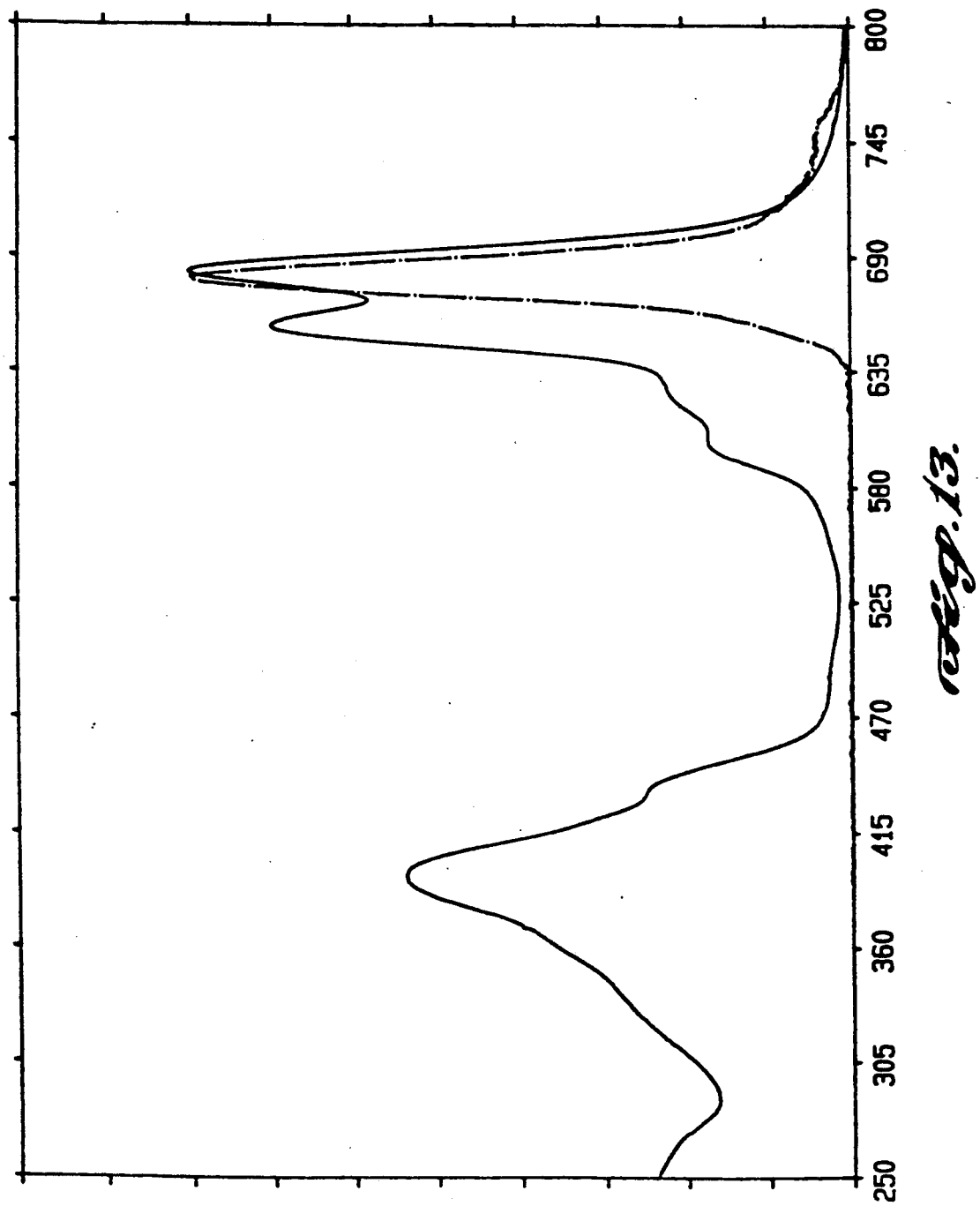
FIG. 13 shows the absorbance and emission spectra of aluminum 20-phenyl tetrabenztriazaporphyrin sulfonate, 13, in water.

Two novel, water soluble aluminum tetrabenztriazaporhphyrins are also described. These compounds are derived from phthalonitrile and are therefore unsubstituted. Reaction of methylmagnesium bromide with phthalonitrile and subsequent aluminum incorporation produced aluminum 20-H TBTAP. Similar reaction of phthalonitrile with benzylmagnesium bromide followed by the incorporation of aluminum gave aluminum 20-phenyl TBTAP. Both of these derivatives were rendered reactive to reactive groups on biological entities (e.g., —OH, —NH$_2$, —SH) by treatment with chlorosulfonic acid. Hydrolysis of the reactive sulfonyl chloride provides the corresponding sulfonates, aluminum 20-H TBTAP sulfonate, 12, and aluminum 20-phenyl TBTAP sulfonate, 13. The absorbance and emission spectra of 12 and 13 in water are presented in FIGS. 12 and 13, respectively. The preparation and spectral summary are provided in Example 4.

ALUMINUM PHTHALOCYANINE TETRAQUATERNARY AMMONIUM DERIVATIVE

Two novel, cationic phthalocyanines, 14a and 14b, are also described. In addition to negatively charged, water soluble aluminum phthalocyanine derivatives, positively charged derivatives are presented. Unlike the aforementioned carboxylated and sulfonated phthalocyanines, the trimethyl ammonium functionalized phthalocyanines were found to be nonfluorescent in water despite their great water solubility. Examination of the absorbance spectra indicated a high degree of aggregation. We found, however, that disaggregation of the cationic fluorophore was achieved in the presence of an anionic surfactant (sodium dodecylsulfate, SDS; typical concentration, about 0.01M). Accompanying the disaggregation was a concomitant increase in the fluorescence emission. Contacting a solution of the aggregate fluorophore with RNA resulted in a similar fluorescent enhancement. The absorbance and emission spectra of 14a and b in water and in the presence of RNA are shown in FIGS. 14, 15, 16, and 17. The preparation of 14a and b and RNA binding experiments are presented in Example 5.

In a second aspect of this invention, there are disclosed derivatives of the phthalocyanines and tetrabenztriazaporphyrins in which 1–4 of the benzo rings of formula I contains one or two N atoms. When two N atoms are contained per benzo group or groups, they will generally be in a pyrazine relationship (i.e. in the 1,4 positions of the benzo ring). While both phthalocyanine and tetrabenztriazaporphyrin pyridine/pyrazine derivatives are contemplated, Z in formula I is preferably N. $R_2$ may be attached to a meso carbon, in which case the benzo rings of the macrocycle will each have an $R_1$ group attached thereto.

SPECTRAL PROPERTIES OF PHTHALOCYANINES, TETRABENZTRIAZAPORPHYRINS AND PYRAZINE AND PYRIDINE DERIVATIVES THEREOF

The emission wavelength (685 nm) of the trisulfonate derivative of aluminum phthalocyanine, 1, elicited by excitation at 350 nm, is red-shifted from the emissions of endogenous fluorophores in physiological solutions. The red emission wavelength of 1 is one of the greatest advantages of this fluorophore. Since emission is shifted away from that of endogenous fluorescence (400–600 nm), background is reduced. Reduction of background leads to a higher signal-to-background ratio and greater sensitivity. This advantage may be realized regardless of where excitation is effected so long as there is absorbance at the excitation wavelength. Excitation of 1 at 325 nm (helium cadmium laser), around 350 nm (Hg lamp source or argon ion laser), 633 nm (helium neon laser), 647 nm (krypton ion laser), or 670 nm (diode laser) leads to emission at 685 nm.

Excitation of 1 at 325 nm or approximately 350 nm leads to emission with more than a 300 nm Stokes' shift. This Stokes' shift can lead to further reduction in background and greater sensitivity. Fluorescence measurements indicate that aluminum phthalocyanine trisulfonate 1 is detectable at concentrations as low as $10^{-15}$M. Linear dynamic range studies indicate a working range of over nine decades and superior detection limits when compared to fluorescein and rhodamine B. Red emission of 1 coupled with the advantage of a large Stokes' shift leads to a 100-fold increase in signal-to-background relative to that of fluorescein.

The application of these reagents to simultaneous, multicomponent fluorescence analysis such as nucleic acid sequence analysis, flow cytometry, immunoassays, or nucleic acid probe assays requires the formation of a family of derivatives. These derivatives must be water soluble, have common excitation wavelengths yet emit at different wavelengths. In addition, the emission bandwidths of each derivative must be narrow (full width at half maximum (FWHM)<40 nm) and resolvable from other members of the family.

Aluminum phthalocyanine (AlPc) based fluorophores in particular have several advantages over dyes currently used for all of these applications.

First, emission spectra of AlPc derivatives suffer less background interference. Interferences attributable to Rayleigh, Tyndall or Raman scatter can be reduced by more than 100 fold due to the large Stokes' shift (>about 300 nm) and long wavelength emission properties of phthalocyanines. Aluminum phthalocyanines emit in the red (>680 nm) at wavelengths beyond endogenous fluorescence (400–600 nm). By contrast, the fluorescein and rhodamine derivatives currently marketed for nucleic acid sequence analysis, flow cytometry, immunoassay and nucleic acid probe assays have only 20–40 nm Stokes' shifts and emit at wavelengths less than 550 nm.

Second, aluminum phthalocyanine based fluorophores have greater separation between emission wavelength maxima. The range of emission maxima for known fluorescein families is only 21 nm with a typical separation of 6 nm between each dye. In contrast, the phthalocyanine family spans about 50 nm with an average separation between family members of greater than 15 nm.

Third, aluminum phthalocyanine based fluorophores have sharp emission bands. The full width at half maximum for fluorescein based dyes ranges from about 32–37 nm with significant red tailing. By comparison, phthalocyanine based fluorophores have bandwidths from about 21–30 nm (with the exception of 7, FWHM=39 nm) with little red tailing.

In summary, all of these properties make aluminum phthalocyanine based fluorophores ideal candidates for multicomponent analysis with application to nucleic acid sequence analysis, flow cytometry, immunoassays, and nucleic acid probe assays. Generally, to realize this potential, the aluminum phthalocyanine based fluorophores must be monomerically tethered.

Figure 18:
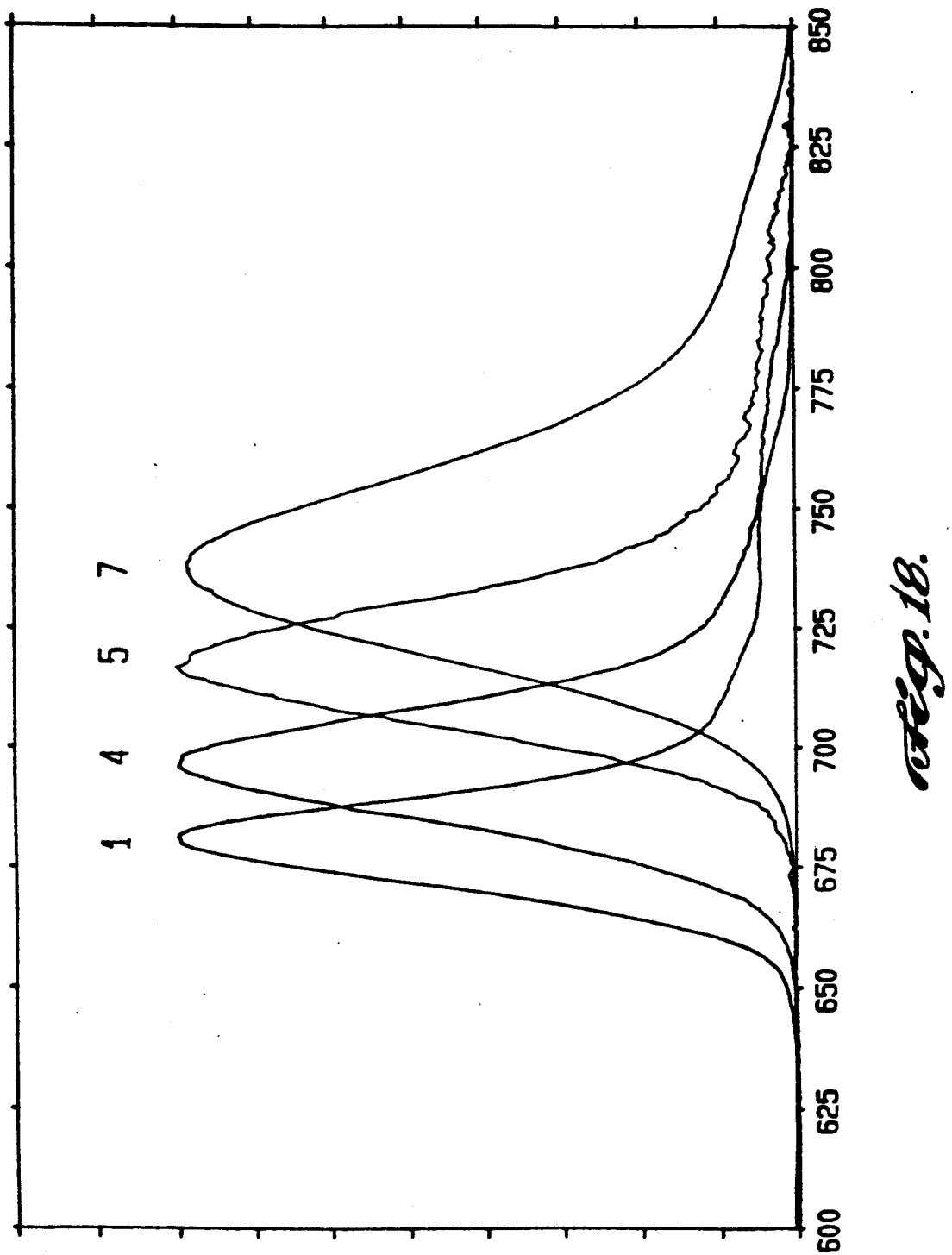
FIG. 18 compares the emission spectra in water of four aluminum phthalocyanine sulfonates, 1, 4, 5, and 7, suitable for DNA sequence analysis.

The emission spectra of four aluminum phthalocyanine sulfonates (1, 4, 5, 7) selected for nucleic acid sequence analysis are presented in FIG. 18.

As noted above, fluorescence emission of phthalocyanines and TBTAPs may be enhanced by rendering the fluorophores monomeric rather than aggregated. The degree of monomerism of a metallophthalocyanine or TBTAP in aqueous solution is a function of the metal. Divalent metals which cannot bear axial ligands tend to stack and exhibit reduced monomerism. Trivalent and greater metals are less prone toward aggregation due to axial ligation and are therefore more fluorescent in solution. The most preferred metals for fluorescent reagents are therefore aluminum, gallium, scandium, silicon, germanium, and tin.

Metallophthalocyanines and TBTAPs suitable for magnetic resonance imaging applications would bear paramagnetic metals such as iron, manganese, and gadolinium. Here the metals are in the plus three oxidation state.

Metallophthalocyanines and TBTAPs suitable for radioactive imaging and therapeutic applications would bear radioisotopes of metals such as copper, cobalt, gallium, and technetium. The radionuclides are gamma-emitters and are sensitive imaging probes.

In connection with U.S. Ser. No. 366,971, filed Jun. 14, 1989, which is incorporated by reference herein, we discovered an empirical relationship between the spectroscopic properties (in terms of the relative heights of the maximum blue and red absorbance peaks) of these compounds to their relative quantum yield.

Early in our investigations of aluminum phthalocyanine sulfonates we observed that the blue absorbance was independent of the state of aggregation and hence the emission yield. In contrast, it was possible to follow the onset of aggregation by changes in the red absorption band. In general, we found that the A(red)/A(blue) ratio decreases with decreasing relative quantum yield. In addition, the behavior of the protein-bound dye is shifted toward a lower relative quantum yield, but very nicely paralleled the free dye in solution. This shift or decrease in quantum yield presumably arises from the hydrophobic nature of the protein environment rather than aggregation quenching.

The most preferred embodiments of the phythalocyanine conjugates of the invention, in terms of monomeric binding, have an A(red)/A(blue)$\geq$2. Such conjugates are readily prepared by Method 3 (see below).

Preferably, the A(red)/A(blue) ratio of the subject conjugates should be $\geq 1.75$, and such conjugates are readily prepared by Method 2.

Phthalocyanine conjugates having A(red)/A(blue) ratios between about 1.5 and 1.75, while suitable for some purposes, have relatively limited sensitivity and so would not be useful.

Conjugates having A(red)/A(blue) ratios of less than 1 are considered to be not suitable for use as fluorescent markers.

The phthalocyanine and tetrabenztriazaporphyrin conjugates of this invention display similar tendencies in terms of their monomeric binding and its relation to the A(red)/A(blue) ratio. However, some of the species disclosed in this invention have much stronger blue absorbances, e.g., compound 4, while others show diminished red absorbance, e.g., compound 12, as monomers in aqueous environments. As a result, the most preferred methods of conjugation yield a range of A(red)/A(blue) from 1.4 to 2.0, depending on the fluorophore.

Exemplary methods for preparing monomeric conjugates are provided below. While these methods are illustrated with aluminum phthalocyanine, it is to be understood that these methods may be applied to other phthalocyanines and to tetrabenztriazaporphyrins, which are disclosed herein. Example 6 describes the coupling of the reactive forms of the red-shifted aluminum phthalocyanines to streptavidin.

Method 1

In the first method, aluminum phthalocyanine may be coupled to a large molecule by a tether linker. The tether linker may be any small bifunctional organic molecule. The tether linker may be 2 to 12 atoms in length. Preferably, the tether linker is 7 to 12 atoms in length and sterically hindered. A long sterically hindered tether ensures that aluminum phthalocyanine is displaced from the biological entity and that individual aluminum phthalocyanine moieties on the large molecule are displaced from one another. The tether linker method may be utilized in conjunction with Methods 2 and 3.

Method 2

Aluminum phthalocyanine may be coupled to large molecules with the use of an aqueous solvent containing a disaggregated organic such as DMF. Use of the disaggregant helps to ensure that aluminum phthalocyanine is bound in a monomeric rather than aggregated state.

Method 3

In a third method, aluminum phthalocyanine may be coupled to large molecules by preincubation of the fluorophore in a disaggregating medium followed by coupling of the fluorophore to a large molecule in an aqueous solvent containing a disaggregating organic solvent such as DMF. The preincubation is preferably performed by mixing a reactive derivative of aluminum phthalocyanine with dimethylformamide for one hour at 30° C. prior to conjugation in a disaggregating medium. The preincubation of fluorophore in a disaggregating organic solvent (e.g., DMF) prior to conjugation in a disaggregating medium is the first disclosure of such a method for generating monomeric conjugates with any fluorescent species including phthalocyanines and porphyrins.

In a third aspect of this invention, there are disclosed cationic phthalocyanine and tetrabenztriazaporphyrin derivatives having formula I, except that $R_2=XYW$, $R_1$, X, and Y being as described above and $W=-N^+D_1D_2D_3$, wherein $D_1-D_3$ are independently H, alkyl, aralkyl or aryl, or W may be a pyridine group. $D_1-D_3$ are preferably H, $C_1-C_{10}$ alkyl, $C_{6-12}$ aralkyl or $C_{6-12}$ aryl. The counterion of these compounds may be any one that is stable and synthetically accessible, and that does not interfere with water solubility or desirable spectral properties. Exemplary negative counterions are $I^-$, $Br^-$, $Cl^-$, $F^-$, borate etc. Exemplary positive counterions are $Ca^{+2}$, $Mg^{+2}$, $Na^+$, $K^+$, quaternary ammonium, etc.

These compounds may be used to detect DNA and RNA, generally by nonspecific binding to the DNA or RNA. Fluorescent detection of the compound bound to the DNA or RNA may then be carried out by standard fluorescent measurement components.

USES OF THE DISCLOSED REAGENTS

In general, the reagents of the first and second aspects of the present invention may be used in combination with binding partners (or ligands) capable of specifically binding with a target substance, particularly an analyte. Once the binding partner specifically binds to an analyte or target of interest, the reagent (referred to as a reporter group in this context) is detected by fluorescence measurement and the presence of and/or amount of the analyte can be determined. The reporter group may be covalently or noncovalently bound to the binding partner and may be attached either prior to or after the analyte and binding partner are caused to interact and bind.

In one embodiment, the reporter group is covalently linked to the binding partner before the binding partner and the analyte are caused to interact and bind.

In another embodiment, the binding partner is caused to interact and bind with the analyte and after binding the reporter group is covalently or noncovalently attached to the binding partner. For example, the binding partner may be conjugated with biotin moieties and the reporter groups may be attached to avidin or streptavidin. Other specific binding pairs may also be used to join the binding partner and the reporter group.

As the binding partner/analyte pairs, the following are representative, preferred embodiments:
nucleic acid probe or primer (e.g., DNA or RNA having 5–10,000 nucleic acid bases)/complementary target DNA or RNA
enzyme/substrate
antibody/antigen (free or bound to other structures, such as a cell)
DNA or protein-binding protein/DNA or protein
lectin/carbohydrate
ligand/ligand binding protein In the above examples, the precise nature of the binding partner and analyte is relatively unimportant. All that is required is that the binding partner and analyte be capable of specific binding to each other and that a reagent as described herein be attachable to the binding partner, either before or after binding to the analyte and either covalently or via a second specific binding pair, e.g., a tightly binding pair such as avidin:biotin, streptavidin:biotin, and maltose binding protein:maltose.

In another preferred embodiment, more than one analyte is determined simultaneously using a corresponding number of binding partners each attached to a different reagent according to the present invention for detection. The different reagents are required to have substantially nonoverlapping emission spectra for separate detection. The combinations of different reagents used in a particular assay may all be of the same general type (e.g. phthalocyanines or TBTAPs) or mixtures of reagent types (e.g. phthalocyanines and TBTAPs). The fluorescence maxima must occur at different wavelengths, preferably separated by at least about 7 nm.

For simultaneous use of fluorescent reagents, the fluorophores must be readily distinguishable for quantitation or quantifiable by ratioing methods.

For Sanger DNA sequencing, a sequencing primer is modified with an amino group at the 5' terminus or each of the four dideoxynucleotides is labeled with one of each of four fluorescent reagents.

For flow cytometry, cell surface antigens expressed by certain subsets of cells may be labeled either directly or indirectly with a fluorescent reagent and antibody or antibody fragment. The number of cell subsets that may be labeled and quantitated is determined by the number of unique fluorescent labels employed.

For immunoassay, each of any number of fluorescent reagents may be attached to a different antigen, antibody, or antibody fragment. For example, a simultaneous thyroid immunoassay test panel may be performed by labeling triiodothyronine (T3) with one fluorescent reagent, thyroxine (T4) with a second fluorescent reagent, and anti-thyroid stimulating hormone (anti-TSH) with a third fluorescent reagent.

For probe assays, any number of fluorescent reagents may be attached to a different nucleic acid probe to perform simultaneous probe analysis. The number of probes that may be detected as the result of a single hybridization step is determined by the number of fluorescent reagents utilized.

In a preferred embodiment, the reagents of the first or second aspects are used to sequence nucleic acid molecules or fragments. The most common approach for DNA sequence analysis is the Sanger dideoxynucleotide sequencing method. For single lane gel DNA sequence analysis, a family of four aluminum phthalocyanine derivatives is required. The derivatives may be used to label either sequencing primers or each of the four dideoxynucleotides (ddNTP's). Surprisingly, although related compounds are known to generate singlet oxygen which can degrade DNA, the present compounds may be effectively used to sequence DNA without degradation.

In the labeled primer strategy, a single primer is labeled with each of four different fluorescent labels. Four separate Sanger sequencing reactions are performed with one of each of the labeled primers, template, sequencing enzyme, deoxynucleotides (dNTP's), and one of each of the four ddNTP's. Once extension and termination are complete, the four reactions are pooled and loaded onto a single lane of sequencing gel. Since each extended primer is terminated with one of the four ddNTP's and labeled with one of the four dyes, the base sequence may be determined by scanning the fluorescence emission directly off the gel.

Alternatively, one may use labeled chain terminators such as dideoxynucleotides rather than labeled primers. Using this approach, all four of the sequencing reactions may be performed in a single vessel and then loaded onto a single lane of the sequencing gel.

The macrocycles involved in the present reagents are larger than the corresponding fluorescein or rhodamine reagents previously used for sequencing and are relatively more planar. As a result, it was unpredictable whether the fluorophore labeled primer of this invention would be compatible with the sequencing enzyme. Researchers at corporations that develop sequencing fluorophores predicted trouble with both sequencing enzyme compatibility and electrophoretic mobility of the sequencing primer and fragments. Empirically, the fluorophore labeled primer was found to be compatible with the sequencing enzyme and the electrophoretic mobility of the dye labeled primer and sequencing fragments is not significantly different from that of the amino modified primer or sequencing fragments.

All of the phthalocyanine labeled primers and the 20H and 20 Ph TBTAP labeled primers have been found to have similar electrophoretic mobility. This was an unexpected result, especially considering that various fluorescein and rhodamine labeled primers have significantly different mobilities. Uniform mobility of primers suggests uniform mobility of fragments. This greatly simplifies the sequencing procedure and analysis, as complex empirical correction factors and equations will not have to be used as extensively or at all.

The present invention also provides kits containing reagents as disclosed herein for performing assays for analytes, for DNA/RNA staining, for DNA sequencing, etc. The kits will generally contain one or more containers of reagents of the present invention, and may contain other chemicals, controls, etc., as may be necessary or desirable. For example, for DNA sequencing kits, there will preferably be four containers of chain terminating dideoxynucleotides conjugated to phthalocyanine or tetrabenztriazaporphyrin moieties, as disclosed herein, additional containers of deoxynucleotides, especially dATP, dTTP, dGTP, and dCTP, a container of a DNA polymerase, a container of template DNA, and a container of a primer DNA. The labeled chain terminating dideoxynucleotides are selected so that their fluorescence emission spectra are distinguishable, i.e. substantially non-overlapping. By "substantially non-overlapping" is meant that the emission spectra have wavelengths of maximum emission that are separated by at least about 7 nm, preferably at least about 10–20 nm.

An alternative DNA sequencing kit may have a container of fluorophorelabeled primer (a reagent of the present invention), containers of deoxynucleotides, e.g., dATP, dTTP, dGTP, dCTP; containers of chain terminators, e.g., ddATP, ddTTP, ddGTP, ddCTP, ddUTP; and a container of a DNA polymerase.

For simultaneous detection of more than one cell type or different markers on different cell subsets using flow cytometry, two or more reagents with maximum spectral resolution are required. Use of at least two different fluorophores having nonoverlapping emission maxima allows the user to perform two color analyses. Two or more color analyses are generally effected by labeling subsets of cells using antibodies specific for each cell type, either indirectly (e.g., via intervening biotin:avidin binding) or directly (i.e., covalently) attached to a fluorescent reagent or dye as disclosed herein.

AIDS testing may be performed by simultaneous analysis of two T cell subsets within a sample of peripheral blood containing lymphocytes. A ratio of T-Helper cells (one color) to T-Suppressor cells (the second color) of other than 2:1 is an indicator of AIDS infection. In conjunction with clinical symptomology, this two color analysis is used for AIDS diagnosis. See Example 16.

Multicomponent immunoassay allows for the simultaneous detection of more than one analyte. Cost and time considerations make this a preferred method for many clinical applications. A single patient sample may be used for detection of a panel of therapeutic drugs, abused drugs, infectious disease agents, hormones or any combination thereof if each of the analytes or antibodies specific for each of the analytes is labeled with a different fluorescent dye.

Multicomponent probe assays enable detection of infectious disease agents, cancers and genetic abnormalities. Since there are probe libraries available for detection of many agents and abnormalities, one would like to have as many fluorophores that may be excited with common wavelengths as possible. In this application, each probe specific for regions of chromosomes associated with disease agents, cancers, or genetic abnormalities (leading to birth defects or genetic diseases) is labeled with a different fluorophore. The cancers treatable or detectable by the present reagents are not necessarily limited and any one for which a therapeutic or diagnostic agent has been developed may potentially be treated or diagnosed using the appropriate fluorophores described herein.

The reagents disclosed herein, particularly those of the first and second aspects, may also be used for photodynamic therapy employing standard methods. See Example 15.

The following Examples are presented to illustrate the advantages of the present invention and to assist one of ordinary skill in making and using the same. The following Examples are not intended in any way to otherwise limit the scope of the disclosure or the protection granted by Letters Patent hereon.

EXAMPLE 1

The Preparation of Aluminum Phthalocyanine Tetraglycolates

Tetrasubstituted phthalocyanines derived from monosubstituted phthalonitriles are necessarily an inseparable mixture of four isomeric products. The product phthalocyanines arise from the differences in orientation of the phthalonitrile during the cyclization process. Cyclization of a 4-substituted phthalonitrile leads to the formation of 2,9,16,23-tetrasubstituted phthalocyanine, as well as three other tetrasubstituted isomers, namely, 2,9,16,24; 2,10,16,24; and 2,9,17,24. Similarly, the cyclization of a 3-substituted phthalonitrile provides the corresponding 1,8,15,22-tetrasubstituted phthalocyanine along with three other tetrasubstituted derivatives, 1,8,15,25; 1,11,15,25; 1,8,18,25. Recognizing this, we have for simplicity designated tetrasubstituted phthalocyanines derived from 3-substituted phthalonitriles as 1,8,15,22 and phthalocyanines derived from 4-substituted phthalonitriles as 2,9,16,23. See FIG. 1 for macrocycle position numbering.

Tetrasubstituted aluminum phthalocyanines may be prepared from monosubstituted phthalonitriles. Nitro displacement from either 3- or 4-nitrophthalonitrile with oxygen or sulfur nucleophiles provide the corresponding phthalonitriles in good yield. The oxygen or sulfur reagent used in the nitro displacement may impart to the phthalocyanine water solubility and tetherability, or may be further elaborated to provide these required properties. Reagents such as hydroxyacetic acid and thioacetic acid may provide appropriately functionalized phthalonitriles directly (X is O or S, Y is $CH_2$, and W is $CO_2H$). Alternatively, tetraoxy or tetrathio substituted phthalocyanines may be treated with an alkylating agent such as methyl bromoacetate to provide the fully functionalized phthalocyanine.

The Preparation of Aluminum Phthalocyanine 2,9,16,23-Tetraglycolic Acid (2)

Treatment of 4-nitrophthalonitrile with neopentyl alcohol and potassium carbonate in dimethylformamide gave 4-neopentoxyphthalonitrile in 90% yield. The metal free 2,9,16,23-tetraneopentoxyphthalocyanine was formed in 40% yield from the corresponding diiminoisoindoline upon reaction of the phthalonitrile with ammonia in methanol followed by reflux in N,N-dimethylaminoethanol. Leznoff, C. C. et al., Can. J. Chem. 63:623–631, 1985.

The metalation of 2,9,16,23-tetraneopentoxyphthalocyanine was accomplished by treatment with ten molar equivalents of trimethyl aluminum in methylene chloride. Smooth conversion occurs at room temperature in eight hours. The product was isolated after an acidic aqueous extractive workup to yield aluminum hydroxy 2,9,16,23-tetraneopentoxyphthalocyanine in essentially quantitative yield.

Cleavage of the neopentyl group is accomplished upon reaction with boron tribromide in benzene as generally disclosed by Rosenthal, I., et al., Photochem. Photobiol. 46(6):959–963, 1987. The cleavage product, aluminum hydroxy 2,9,16,23-tetrahydroxyphthalocyanine, is a versatile intermediate which may be treated with a variety of alkylating agents to provide a family of tetraalkoxy substituted phthalocyanines.

Alkylation of the tetrahydroxy derivative with methyl bromoacetate and potassium carbonate (forty molar equivalents of each) in refluxing methanol affords the tetra methyl ester derivative. The alkylated product may be directly hydrolyzed to the tetracarboxylic acid by heating in a solution of 0.5M methanolic potassium hydroxide. Aluminum hydroxy 2,9,16,23-tetraglycolylphthalocyanine was isolated by precipitation, 2, from an aqueous acid solution.

The Preparation of Aluminum Phthalocyanine 1,8,15,22-Tetraglycolic Acid (3)

The synthesis of aluminum hydroxy 1,8,15,22-tetraglycolylphthalocyanine, 3, was analogous to that described above for 2.

The absorbance and emission spectra in water are shown in FIGS. 3 and 4, respectively. The effect of cetyl trimethlyammonium bromide (CTAB) on the emission spectra of the two isomers is shown in FIG. 5.

Tabulated below is a comparison of the spectral data for 1, 2, and 3 in water.

| Phthalocyanine | Absorbance | Emission | Quantum Yield |
| --- | --- | --- | --- |
| 1 | 673 nm | 683 | 0.60 |
| 2 | 692 | 704 | 0.55 |
| 3 | 720 | 727 | 0.43 |

EXAMPLE 2

The Preparation of Oxygen and Sulfur Substituted Aluminum Phthalocyanine Sulfonates Tetrasubstituted oxygen and sulfur substituted aluminum phthalocyanine sulfonates are described in Example 2. The four tetrasubstituted reagents of Example 2 are prepared from monosubstituted phthalonitriles. The following is a detailed description of the preparation of a family of four aluminum phthalocyanine based reagents. The presentation is organized into sections which detail phthalocyanine preparation, phthalocyanine metalation, reactive phthalocyanine formation, and water soluble phthalocyanine formation. Within each section a detailed procedure is given for one member of the family of four reagents followed by a comment on the procedures for the other three reagents. Any differences in procedure are highlighted.

PHTHALOCYANINE PREPARATION

2,9,16,23-Tetraphenoxyphthalocyanine

To 1.0 g (4.55 mm) 4-phenoxyphthalonitrile in 10 mL 3-methyl-1-butanol was added 5 mL lithium 3-methyl-1-butanoxide (prepared by the dissolution of 10 mg lithium metal in 5 mL of the alcohol). The resulting solution was heated at reflux under nitrogen for six hours. The solvent was removed in vacuo and the crude product was taken up in 50 mL methylene chloride. The solution was washed with 3–50 mL portions 1N aqueous hydrochloric acid, dried over sodium sulfate, filtered and concentrated. The product was then redissolved in 10 mL methylene chloride and precipitated by the addition of 100 mL methanol. The product was collected by filtration, washed with 500 mL methanol, and dried in vacuo. The product, 0.53 g (0.60 mm, 52%), was isolated as a blue powder. The spectral properties are tabulated below.

1,8,15,22-Tetraphenoxyphthalocyanine

In a procedure analogous to that described above, 3-phenoxyphthalonitrile produced 1,8,15,22-tetraphenoxyphthalocyanine in 45% yield. The spectral properties are tabulated below.

2,9,16,23-Tetrathiophenylphthalocyanine

In a procedure analogous to that described above, 4-thiophenylphthalonitrile produced 2,9,16,23-tetrathiophenylphthalocyanine in 51% yield. The spectral properties are tabulated below.

1,8,15,22-Tetrathiophenylphthalocyanine

In a procedure analogous to that described above, 3-thiophenylphthalonitrile produced 1,8,15,22-tetrathiophenylphthalocyanine in 87% yield. In this case, the product was isolated by precipitation from methylene chloride without the addition of methanol. The spectral properties are tabulated below.

The following table summarizes the absorbance and emission wavelengths for the metal free phthalocyanines prepared as described above. The spectra were recorded as methylene chloride solutions.

| Phthalocyanine | Absorbance | Emission | Quantum Yield |
| --- | --- | --- | --- |
| 2,9,16,23 oxy | 700 nm | 705 nm | 0.25 |
| 1,8,15,22 oxy | 716 | 723 | 0.29 |
| 2,9,16,23 thio | 711 | 719 | 0.40 |
| 1,8,15,22 thio | 723 | 738 | 0.26 |

PHTHALOCYANINE METALATION

Trimethylaluminum Metalation Method

Aluminum Hydroxy 2,9,16,23-Tetraphenoxyphthalocyanine

To a solution of 500 mg (0.60 mm) 2,9,16,23-tetraphenoxyphthalocyanine in 200 mL dry methylene chloride under nitrogen at room temperature was added dropwise ten equivalents, 3.0 mL (6.0 mm) of a 2.0M solution of trimethylaluminum in toluene. The reaction mixture was stirred at room temperature for 24 hours and then quenched by the careful addition of 10 mL distilled water followed by 1 mL 1N aqueous hydrochloric acid. The solution was then separated and the organic layer was washed with 3–20 mL portions 1N aqueous hydrochloric acid. The methylene chloride solution was dried over sodium sulfate and concentrated to dryness. The product, aluminum hydroxy 2,9,16,23-tetraphenoxyphthalocyanine, was isolated as a blue solid, 230 mg (0.25 mm, 41%). The spectral properties are tabulated below.

Aluminum Hydroxy 1,8,15,22-Tetraphenoxyphthalocyanine

In a procedure analogous to that described above, aluminum hydroxy 1,8,15,22-tetraphenoxyphthalocyanine was prepared and its spectral data tabulated below.

Aluminum Hydroxy 2,9,16,23-Tetrathiophenylphthalocyanine

In a procedure analogous to that described above, aluminum hydroxy 2,9,16,23-tetrathiophenylphthalocyanine was prepared and its spectral data tabulated below.

Aluminum Hydroxy 1,8,15,22-Tetrathiophenylphthalocyanine

In a procedure analogous to that described above, aluminum hydroxy 1,8,15,22-tetrathiophenylphthalocyanine was prepared and its spectral data tabulated below.

The table below summarizes the absorbance and emission wavelengths and relative quantum yields of the aluminum phthalocyanines prepared as described above. The spectra were recorded in dimethylformamide.

| Phthalocyanine | Absorbance | Emission | Quantum Yield |
| --- | --- | --- | --- |
| 2,9,16,23 oxy | 680 nm | 686 nm | 0.51 |
| 1,8,15,22 oxy | 701 | 703 | 0.25 |
| 2,9,16,23 thio | 687 | 696 | 0.46 |
| 1,8,15,22 thio | 713 | 722 | 0.30 |

Aluminum Triacetylacetonate Metalation Method

Aluminum Acetylacetonate 2,9,16,23-Tetraphenoxyphthalocyanine

To a solution of 2.5 g (2.8 mm) 2,9,16,23-tetraphenoxyphthalocyanine in 50 mL dimethylformamide was added ten equivalents, 9.0 g (28.0 mm) aluminum acetylacetonate. After stirring at room temperature for one hour the solution was diluted with 500 mL methanol and the crude product was collected by filtration, washed with 500 mL methanol and dried in vacuo. Aluminum acetylacetonate 2,9,16,23-tetraphenoxyphthalocyanine, 1.7 g (1.84 mm, 66%), was isolated as a blue powder. The spectral data is tabulated below.

Aluminum Acetylacetonate 1,8,15,22-Tetraphenoxyphthalocyanine

In a procedure analogous to that described above, aluminum acetylacetonate 1,8,15,22-tetraphenoxyphthalocyanine was prepared in 59% yield. The spectral data are tabulated below.

| Phthalocyanine | Absorbance | Emission | Quantum Yield |
|---|---|---|---|
| 2,9,16,23 | 680 nm | 686 nm | 0.27 |
| 1,8,15,22 | 697 | 701 | 0.20 |

REACTIVE PHTHALOCYANINE FORMATION

Aluminum Hydroxy 2,9,16,23-Tetraphenoxyphthalocyanine Sulfonyl Chloride

To 96 mg (0.104 mm) aluminum hydroxy 2,9,16,23-tetraphenoxyphthalocyanine was added 1.0 mL chlorosulfonic acid. The mixture was stirred to effect dissolution, sealed under argon, and immersed in a preequilibrated oil bath at 100° C. The solution was stirred at 100° C. for one hour, cooled to 0° C., and quenched by the gradual addition of the crude reaction mixture to 10 g of ice. The solid product was collected by filtration, washed with 2-20 mL portions of distilled water and 2-20 mL portions diethyl ether. The solid was then transferred to a flask and pulverized to a fine solid in 20 mL diethyl ether, collected by filtration, washed with 2-20 mL portions diethyl ether, and dried under vacuum. Aluminum hydroxy 2,9,16,23-tetraphenoxyphthalocyanine sulfonyl chloride was isolated in 89% yield. Spectral data are tabulated below.

Aluminum Hydroxy 1,8,15,22-Tetraphenoxyphthalocyanine Sulfonyl Chloride

In a procedure analogous to that described above except with a reaction temperature of 70° C., aluminum hydroxy 1,8,15,22-tetraphenoxyphthalocyanine sulfonyl chloride was isolated in 54%. Spectral data are tabulated below.

Aluminum Hydroxy 2,9,16,23-Tetrathiophenylphthalocyanine Sulfonyl Chloride

In a procedure analogous to that described above with a reaction temperature of 100° C., aluminum hydroxy 2,9,16,23-tetrathiophenylphthalocyanine sulfonyl chloride was isolated in quantitative yield. Spectral data are tabulated below.

Aluminum Hydroxy 1,8,15,22-Tetrathiophenylphthalocyanine Sulfonyl Chloride

In a procedure analogous to that described above except with a reaction temperature of 80° C., aluminum hydroxy 1,8,15,22-tetrathiophenylphthalocyanine sulfonyl chloride was isolated in 73% yield. Spectral data are tabulated below.

The table below summarizes the maximum absorbance and emission wavelengths for the reactive sulfonyl chloride derivatives in dimethylformamide solution prepared as described above.

| Phthalocyanine | Absorbance | Emission | Quantum Yield |
|---|---|---|---|
| 2,9,16,23 oxy | 684 nm | 693 nm | 0.41 |
| 1,8,15,22 oxy | 704 | 708 | 0.14 |
| 2,9,16,23 thio | 697 | 703 | 0.38 |
| 1,8,15,22 thio | 715 | 724 | 0.17 |

WATER SOLUBLE PHTHALOCYANINE FORMATION

Aluminum Hydroxy 2,9,16,23-Tetraphenoxyphthalocyanine Sulfonate (4)

A solution of 10 mg of aluminum hydroxy 2,9,16,23-tetraphenoxyphthalocyanine sulfonyl chloride in 10 mL distilled water was stirred vigorously at room temperature for 48 hours. The resulting solution was concentrated to dryness to yield aluminum hydroxy 2,9,16,23-tetraphenoxyphthalocyanine sulfonate, 4, in quantitative yield. The absorbance and emission spectra of 4 in water are presented in FIGS. 6 and 7, respectively. Spectral data are tabulated below.

Aluminum Hydroxy 1,8,15,22-Tetraphenoxyphthalocyanine Sulfonate (5)

In a procedure analogous to that described above, aluminum hydroxy 1,8,15,22-tetraphenoxyphthalocyanine sulfonate, 5, was isolated in quantitative yield. The absorbance and emission spectra of 5 in water are presented in FIGS. 6 and 7, respectively. Spectral data are tabulated below.

Aluminum Hydroxy 2,9,16,23-Tetrathiophenylphthalocyanine Sulfonate (6)

In a procedure analogous to that described above, aluminum hydroxy 2,9,16,23-tetrathiophenylphthalocyanine sulfonate, 6, was isolated in quantitative yield. The absorbance and emission spectra of 6 in water are presented in FIGS. 8 and 9, respectively. Spectral data are tabulated below.

Aluminum Hydroxy 1,8,15,22-Tetrathiophenylphthalocyanine Sulfonate (7)

In a procedure analogous to that described above, aluminum hydroxy 1,8,15,22-tetrathiophenylphthalocyanine sulfonate, 7, was isolated in quantitative yield. The absorbance and emission spectra of 7 in water are presented in FIGS. 8 and 9, respectively. Spectral data are tabulated below.

Tabulated below are the maximum absorbance and emission wavelengths of the oxygen and sulfur substituted aluminum phthalocyanine sulfonate derivatives in water prepared as described above.

| Compound No. | Phthalocyanine | Absorbance | Emission | Quantum Yield |
|---|---|---|---|---|
| 4 | 2,9,16,23 oxy | 685 nm | 697 nm | 0.49 |
| 5 | 1,8,15,22 oxy | 707 | 717 | 0.20 |
| 6 | 2,9,16,23 thio | 695 | 708 | 0.28 |
| 7 | 1,8,15,22 thio | 719 | 733 | 0.10 |

Aluminum Acetylacetonate Tetraphenoxyphthalocyanine Sulfonates

Water soluble aluminum phthalocyanine sulfonates were prepared from aluminum acetylacetonate 2,9,16,23- and 1,8,15,22-tetraphenoxyphthalocyanines as described above for the corresponding axial hydroxy compounds. The absorbance and emission wavelengths as well as quantum yields in water are tabulated below.

| Phthalocyanine | Absorbance | Emission | Quantum Yield |
|---|---|---|---|
| 2,9,16,23 oxy | 641 nm | 688 nm | 0.003 |
| 1,8,15,22 oxy | 665 | 706 | 0.026 |

The spectral data summarized above for the acetylacetonate ligated aluminum phthalocyanine sulfonates contrasts significantly with the data for the corresponding hydroxylated derivatives. The wavelengths of fluorescence emission of the acetylacetonates are roughly 10 nm blue shifted relative to their hydroxy analogs. The blue shift limits their utility in multicomponent analysis when used in conjunction with the parent, aluminum phthalocyanine sulfonate, which emits at 684 nm. The ideal family of fluorophores for multicomponent analysis will have spectrally resolved emission bands. The emission of the 2,9,16,23 isomer with axial acetylacetonate at 688 nm is too close to the parent, 684 nm, to be effectively resolved. More importantly, the fluorescent quantum yields for the acetylacetonate derivatives are drastically reduced to the point where their utility as fluorophores is greatly impaired.

For the above reasons, the preferred embodiment of aluminum phthalocyanine sulfonates employs axial hydroxy rather than acetylacetonate ligands.

EXAMPLE 3

The Preparation of Oxygen and Sulfur Substituted Aluminum Tetrabenztriazaporphyrins Tetrasubstituted oxygen and sulfur substituted aluminum tetrabenztriazaporphyrins are described in Example 3. The four tetrasubstituted reagents of Example 3 are prepared from monosubstituted phthalonitriles. The following is a detailed description of the preparation of a family of four aluminum tetrabenztriazaporphyrin based reagents. The presentation is organized into sections which detail tetrabenztriazaporphyrin preparation, metalation, reactive derivative formation, and water-soluble derivative formation. Within each section a detailed procedure is given followed by a comment on the procedures for the other three reagents. Any differences in procedure are highlighted.

TETRABENZTRIAZAPORPHYRIN PREPARATION

20-Phenyl 2,9,16,23-Tetraphenoxytetrabenztriazaporphyrin

To a solution of 1.00 g (4.59 mm) 4-phenoxyphthalonitrile in 4 mL dry tetrahydrofuran was added 10 mL dry diethyl ether. The mixture was cooled to 0° and 4.6 mL of 1.0M benzylmagnesium chloride (4.6 mm, 1.0 equivalent) in diethyl ether was added. The mixture was stirred under argon at room temperature for 2 hour. The mixture was then concentrated to dryness and the purple residue was diluted with 25 mL quinoline and stirred at 200°–210° for 4 hours. The solvent was distilled under vacuum. The resulting residue was treated with stirring with 30 mL glacial acetic acid at 90° for 2 hour. The reaction mixture was diluted with 200 mL methylene chloride and washed first with 3–200 mL portions saturated aqueous sodium bicarbonate and then with 200 mL 5% v/v aqueous hydrochloric acid. The organic phase was dried over sodium sulfate, filtered and concentrated. The crude reaction product was chromatographed on silica gel eluting with chloroform. The fractions containing the desired product were combined, concentrated and twice more chromatographed on silica gel, eluting with 85% chloroform in hexane to afford 204 mg (19%) 20-phenyl 2,9,16,23-tetraphenoxytetrabenztriazaporphyrin as a deep blue-green solid. Silica thin layer chromatography eluting with 65% methylene chloride in hexane gave a homogeneous product with an $R_f$ of 0.54. Spectral data are tabulated below.

20-Phenyl 1,8,15,22-Tetraphenoxytetrabenztriazaporphyrin

In a procedure analogous to that described above, 3-phenoxyphthalonitrile was converted to 20-phenyl 1,8,15,22-tetrabenztriazaporphyrin after heating in quinoline for 40 hours. The product was purified by chromatography on silica gel eluting with methylene chloride followed by crystallization from a methylene chloride: hexane (1:1) solution. The product was isolated in 6% yield as a deep green solid with an $R_f$ of 0.60 on silica eluting with methylene chloride. Spectral data are tabulated below.

20-Phenyl 2,9,16,23-Tetrathiophenylbenztriazaporphyrin

In a procedure analogous to that described above for 20-phenyl 2,9,16,23-tetraphenoxytetrabenztriazaporphyrin, 4-thiophenylphthalonitrile was converted to 20-phenyl 2,9,16,23-tetrathiophenyltetrabenztriazaporphyrin after heating in quinoline for 20 hours. After initial chromatography eluting with chloroform, the fractions containing the desired product were combined and twice rechromatographed on silica eluting with 55% chloroform in hexane. The product was isolated in 21% yield as a deep green solid with an $R_f$ of 0.72 on silica eluting with 65% methylene chloride in hexane. Spectral data are tabulated below.

20-Phenyl 1,8,15,22-Tetrathiophenyltetrabenztriazaporphyrin

In a procedure analogous to that described above for 20-phenyl 1,8,15,22-tetraphenoxytetrabenztriazaporphyrin, 3-thiophenylphthalonitrile was converted to 20-phenyl 1,8,15,22-tetrathiophenoxytetrabenztriazaporphyrin. After initial chromatography on silica eluting with methylene chloride, the product was twice more chromatographed eluting with 50% methylene chloride in hexane. Further purification by crystallization from a methylene chloride: hexane (1:1) solution afforded the product in 11% yield as a deep green solid. Silica thin layer chromatography eluting with 65% methylene chloride in hexane gave an $R_f$ of 0.70. Spectral data are tabulated below.

Tabulated below are the absorbance data for the oxygen and sulfur substituted 20-phenyl tetrabenztriazaporphyrin derivatives prepared as described above. The spectra were recorded in methylene chloride solution.

| Tetrabenztriazaporphyrin | Absorbance |
|---|---|
| 2,9,16,23 oxy | 656, 694 nm |
| 1,8,15,22 oxy | 676, 712 |
| 2,9,16,23 thio | 666, 704 |
| 1,8,15,22 thio | 694, 728 |

TETRABENZTRIAZAPORPHYRIN METALATION

Aluminum Hydroxy 20-Phenyl 2,9,16,23-Tetraphenoxytetrabenztriazaporphyrin

To a solution of 200 mg (0.209 mm) 20-phenyl 2,9,16,23-tetrabenztriazaporphyrin in 15 mL methylene chloride was added 2.0 mL 2.0M trimethylaluminum (4.00 mm, 19 equivalents) in toluene at 0°. The mixture was stirred at room temperature for two hours. The mixture was then cooled to 0° and carefully treated dropwise with 1 mL of distilled water. The mixture was stirred for 10 minutes and treated dropwise with 2 mL 10% V/V aqueous hydrochloric acid. The reaction mixture was stirred for 5 minutes, treated with 20 mL 10% V/V aqueous hydrochloric acid and stirred for one hour. The mixture was diluted with 50 mL methylene chloride and washed with 50 mL 5% V/V aqueous hydrochloric acid. The organic phase was drived over sodium sulfate, filtered and concentrated to afford 183 mg (88%) aluminum hydroxy 20-phenyl 2,9,16,23-tetraphenoxytetrabenztriazaporphyrin as a deep blue-green solid.

Aluminum Hydroxy 20-Phenyl 1,8,15,22-Tetraphenoxytetrabenztriazaporphyrin

In a procedure analogous to that described above, aluminum hydroxy 20-phenyl 1,8,15,22-tetraphenoxytetrabenztriazaporphyrin was isolated in 90% yield.

Aluminum Hydroxy 20-Phenyl 2,9,16,23-Tetrathiophenyltetrabenztriazaporphyrin In a procedure analogous to that described above, aluminum hydroxy 20-phenyl 2,9,16,23-tetrathiophenyltetrabenztriazaporphyrin was isolated in 96% yield.

Aluminum Hydroxy 20-Phenyl 1,8,15,22-Tetrathiophenyltetrabenztriazaporphyrin In a procedure analogous to that described above, aluminum hydroxy 20-phenyl 1,8,15,22-tetrathiophenyltetrabenztriazaporphyrin was isolated in 97% yield.

Tabulated below are the absorbance wavelengths of the aluminum axial methyl derivatives in methylene chloride solution and the emission wavelengths of the axial hydroxy derivatives in tetrahydrofuran. The quantum yields were determined in tetrahydrofuran.

| TBTAP | Absorbance | Emission | Quantum Yield |
| --- | --- | --- | --- |
| 2,9,16,23 oxy | 656, 694 nm | 690 nm | 0.40 |
| 1,8,15,22 oxy | 676, 712 | 704 | 0.25 |
| 2,9,16,23 thio | 666, 704 | 701 | 0.26 |
| 1,8,15,22 thio | 694, 728 | 722 | 0.19 |

REACTIVE TETRABENZTRIAZAPORPHYRIN FORMATION

The sulfonyl chloride derivatives of the four tetrasubstituted aluminum hydroxy 20-phenyl tetrabenztriazaporphyrins were prepared by treatment with chlorosulfonic acid as described previously for the corresponding aluminum phthalocyanines in Example 2.

WATER SOLUBLE TETRABENZTRIAZAPORPHYRIN FORMATION

Hydrolysis of the above sulfonyl chloride derivatives in a procedure analogous to that described previously for the corresponding aluminum phthalocyanines in Example 2, provided four, water soluble aluminum hydroxy 20-phenyl tetrabenztriazaporphyrin sulfonates. The absorbance and emission wavelengths of the four tetrabenztriazaporphyrins in water along with the quantum yields. The emission spectra for 8, 9, 10, and 11 are presented in FIGS. 10 and 11, respectively.

| Compound No. | TBTAP | Absorbance | Emission | Quantum Yield |
| --- | --- | --- | --- | --- |
| 8 | 2,9,16,23 oxy | 664, 692 nm | 695 nm | 0.43 |
| 9 | 1,8,15,22 oxy | 676, 704 | 711 | 0.22 |
| 10 | 2,9,16,23 thio | 690, 713 | 717 | 0.14 |
| 11 | 1,8,15,22 thio | 691, 715 | 728 | 0.06 |

EXAMPLE 4

The Preparation of Aluminum Tetrabenztriazaporphyrin Sulfonates

Aluminum tetrabenztriazaporphyrins sulfonates substituted at position twenty with either hydrogen, 12, or phenyl, 13, are described in Example 4. These water solution and reactive derivatives have performance characteristics similar to the aluminum phthalocyanines sulfonates and possess the optical properties of the aluminum tetrabenztriazaporphyrins. The following is a detailed description of the preparation of these compounds. The presentation is organized into sections which detail tetrabenztriazaporphyrin preparation, metalation, reactive TBTAP preparation, and water soluble TBTAP preparation. Within each section a detailed procedure is given for the 20-hydrogen derivative followed by a comment on the procedure for the 20-phenyl derivative.

TETRABENZTRIAZAPORPHYRIN PREPARATION

Magnesium 20-H Tetrabenztriazaporphyrin

To a suspension of 5.0 g (39.1 mm) phthalonitrile in 25 mL diethyl ether was added dropwise 1.1 equivalents, 14.3 mL (43.0 mm) 3.0M methylmagnesium bromide in diethyl ether. The resulting solution was stirred at room temperature under nitrogen for two hours. The ether was removed under vacuum and 25 mL quinoline was added. The reaction solution was heated at 200° under nitrogen for 16 hours. The solution was cooled and diluted with 1 L methylene chloride to precipitate the crude product. The crude product was collected by filtration and extracted with methanol in a Soxhlet extractor until the extract was colorless. The product, the Soxhlet residue, was isolated as a blue solid, 2.95 g (5.48 mm, 56%). Spectral data are tabulated below.

Magnesium 20-Phenyl Tetrabenztriazaporphyrin

In a procedure analogous to that described above, magnesium 20-phenyl tetrabenztriazaporphyrin was prepared. The product was isolated by dilution of the quinoline reaction mixture with 500 mL distilled water. The crude product was collected by filtration and dried in vacuo. The product was purified by chromatography on silica eluting with hexane:tetrahydrofuran (1:1). Spectral data are tabulated below.

Tabulated below are the absorbance wavelengths of the magnesium tetrabenztriazaporphyrin derivatives in tetrahydrofuran prepared as described above.

| TBTAP | Absorbance |
|---|---|
| 20-H | 645, 665 nm |
| 20-Ph | 648, 670 |

20-H Tetrabenztriazaporphyrin

A solution of 1.0 g (1.86 mm) magnesium 20-H tetrabenztriazaporphyrin in 10 mL trifluoroacetic acid was stirred for 16 hours. The solution was diluted with 100 mL distilled water and the solid was collected by filtration. The product was washed with 500 mL distilled water, 500 mL methanol and dried in vacuo. 20-H Tetrabenztriazaporphyrin, 280 mg (0.54 mm, 29%), was isolated as a blue solid. Spectral data are tabulated below.

20-Phenyl Tetrabenztriazaporphyrin

A solution of 1.0 g (1.63 mm) magnesium 20-phenyl tetrabenztriazaporphyrin in 10 mL acetic acid was heated at reflux for 1 hour. The solution was cooled and diluted with 100 mL distilled water. The product was collected by filtration and washed with 500 mL distilled water and dried in vacuo. 20-Phenyl tetrabenztriazaporphyrin, 115 mg (0.22 mm, 14%), was isolated as a blue solid. Spectral data are tabulated below.

Tabulated below are the absorbance wavelengths of the tetrabenztriazaporphyrin derivative in tetrahydrofuran prepared as described above.

| TBTAP | Absorbance |
|---|---|
| 20-H | 640, 682 nm |
| 20-Ph | 643, 684 |

TETRABENZTRIAZAPORPHYRIN METALATION

Aluminum 20-H Tetrabenztriazaporphyrin

A solution of 100 mg (0.195 mm) 20-H tetrabenztriazaporphyrin in 5 mL quinoline was treated with ten equivalents, 260 mg (1.95 mm) aluminum trichloride under nitrogen. The solution was heated at 200° for two hours, cooled, and diluted with 100 mL methylene chloride. The precipitated product was collected by filtration and washed with 500 mL methylene chloride. Aluminum 20-H tetrabenztriazaporphyrin, 85 mg (0.15 mm, 76%), was isolated as a purple solid. Spectral data are tabulated below.

Aluminum 20-Phenyl Tetrabenztriazaporphyrin

To 115 mg (0.224 mm) 20-phenyl tetrabenztriazaporphyrin in 20 mL methylene chloride was added ten equivalents, 1.12 mL (2.24 mm) 2.0M trimethylaluminum in toluene. The solution was stirred at room temperature under nitrogen for two hours and then carefully quenched with 1 mL distilled water followed by 1 mL 1N aqueous hydrochloric acid. The organic solution was extracted with 3–20 mL portions 1N aqueous hydrochloric acid, dried over sodium sulfate, and concentrated. Aluminum 20-phenyl tetrabenztriazaporphyrin, 85 mg (0.15 mm, 68%), was isolated as a blue solid. Spectral data are tabulated below.

Tabulated below are the absorbance and emission wavelengths, and quantum yields of the aluminum tetrabenztriazaporphyrins in dimethylformamide prepared as described above.

| TBTAP | Absorbance | Emission | Quantum Yield |
|---|---|---|---|
| 20-H | 649, 670 nm | 672 nm | 0.69 |
| 20-Ph | 656, 681 | 680 | 0.56 |

REACTIVE TETRABENZTRIAZAPORPHYRIN FORMATION

Aluminum 20-H Tetrabenztriazaporphyrin Sulfonyl Chloride

A solution of 150 mg (0.26 mm) aluminum 20-H tetrabenztriazaporphyrin in 5 mL chlorosulfonic acid was heated at 150° for two hours under nitrogen. The mixture as cooled and carefully quenched on 5 g ice. The product was collected by filtration, washed with 20 mL distilled water, 100 mL diethyl ether, and dried in vacuo. Aluminum 20-H tetrabenztriazaporphyrin sulfonyl chloride, 180 mg (0.189 mm, 73%), was isolated as a blue powder. Spectral data are tabulated below.

Aluminum 20-Phenyl Tetrabenztriazaporphyrin Sulfonyl Chloride

In a procedure analogous to that described above, aluminum 20-phenyl tetrabenztriazaporphyrin sulfonyl chloride was isolated in 72% yield. Spectral data are tabulated below.

Tabulated below are the absorbance wavelengths for the aluminum tetrabenztriazaporphyrin sulfonyl chloride derivatives in dimethylformamaide prepared as described above.

| TBTAP | Absorbance |
|---|---|
| 20-H | 655, 677 nm |
| 20-Ph | 657, 683 |

WATER SOLUBLE TETRABENZTRIAZAPORPHYRIN FORMATION

Aluminum 20-H Tetrabenztriazaporphyrin Sulfonate (12)

A solution of 9.6 mg aluminum 20-H tetrabenztriazaporphyrin sulfonyl chloride in 5.0 mL distilled water was stirred at room temperature for 48 hour. Concentration in vacuo gave aluminum 20-H tetrabenztriazaporphyrin sulfonate in quantitative yield. The absorbance and emission spectra in water are presented in FIG. 12. Spectral data are tabulated below.

Aluminum 20-Phenyl Tetrabenztriazaporphyrin Sulfonate (13)

In a procedure analogous to that described above, aluminum 20-phenyl tetrabenztriazaporphyrin sulfonate was isolated in quantitative yield. The absorbance and emission spectra in water are presented in FIG. 13. Spectral data are tabulated below.

Tabulated below are the absorbance and emission wavelengths of the aluminum tetrabenztriazaporphyrin sulfonates in water prepared as described above. The quantum yields are also included.

| TBTAP | Absorbance | Emission | Quantum Yield |
|---|---|---|---|
| 20-H | 649, 667 nm | 672 nm | 0.67 |
| 20-Ph | 653, 672 | 681 | 0.59 |

EXAMPLE 5

The Preparation of Phthalocyanine Tetraquaternary Ammonium Derivatives

Exemplary cationic phthalocyanines are presented in Example 5The derivatives in Example 5 satisfy formula I where M is either $H_2$ or aluminum, each $R_1$ is —XYW, X is oxygen, Y is ethylene (—$CH_2CH_2$—), W is trimethylammonium iodide, Z is nitrogen, and $R_2$ is —XYW, —YW, or —W. The positively charged tetrasubstituted phthalocyanines are prepared from monosubstituted phthalonitriles.

The phthalocyanine precursor, 4-dimethylaminoethanoxyphthalonitrile, was prepared by displacement of nitro from 4-nitrophthalonitrile with 2-dimethylaminoethanol. Formation of the diiminoisoindoline and subsequent cyclization resulted in the metal free tetrasubstituted phthalocyanine. The amino groups were quaternized with methyl iodide. Aluminum was incorporated by treatment with aluminum triacetylacetonate. The aluminum phthalocyanine was rendered water soluble by alkylation with methyl iodide to provide the tetraquaternary ammonium compound 14b.

Figure 14:
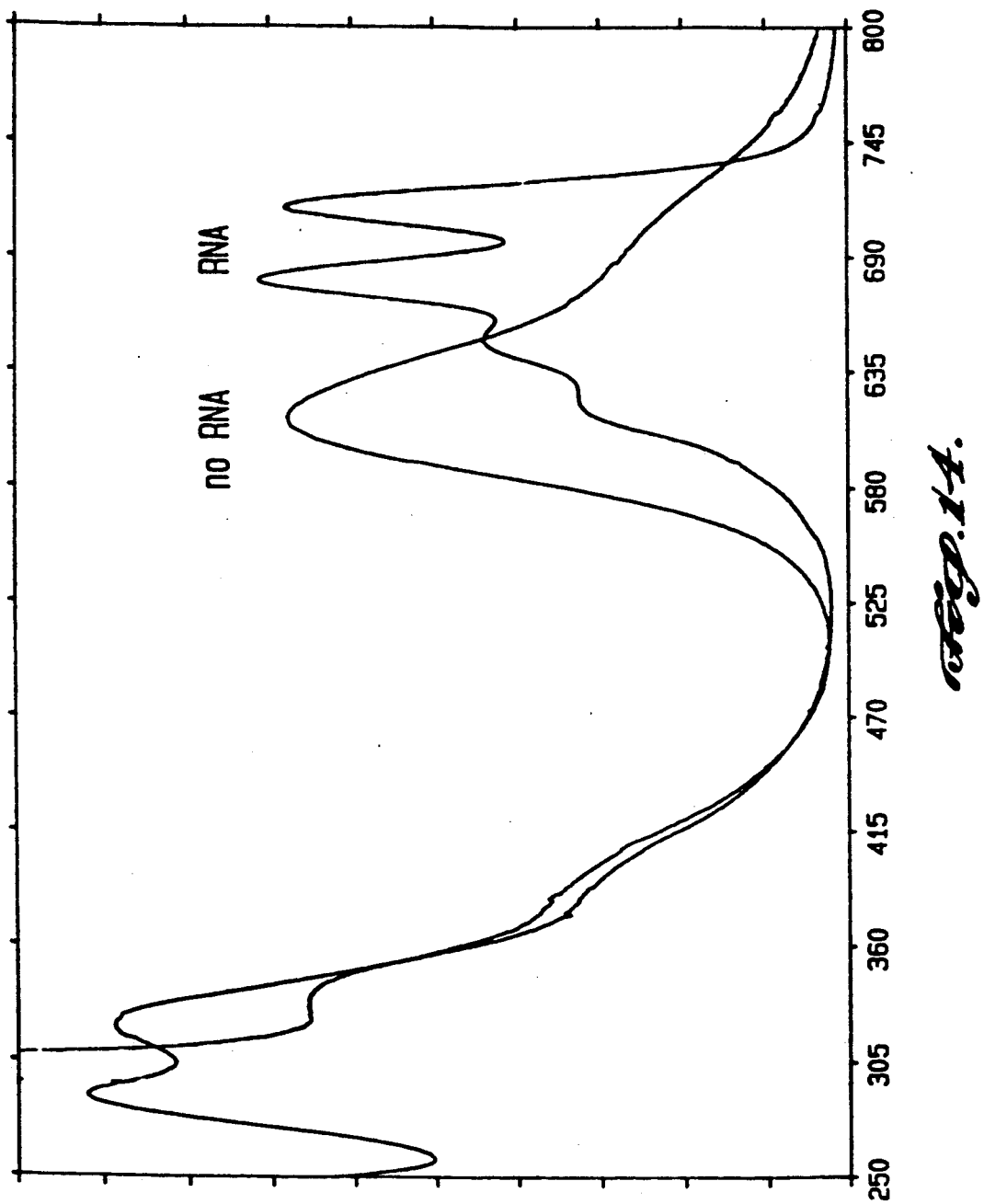
FIG. 14 compares the absorbance spectra of the metal free phthalocyanine cationic fluorophore, 14a, in water with and without RNA.
Figure 15:
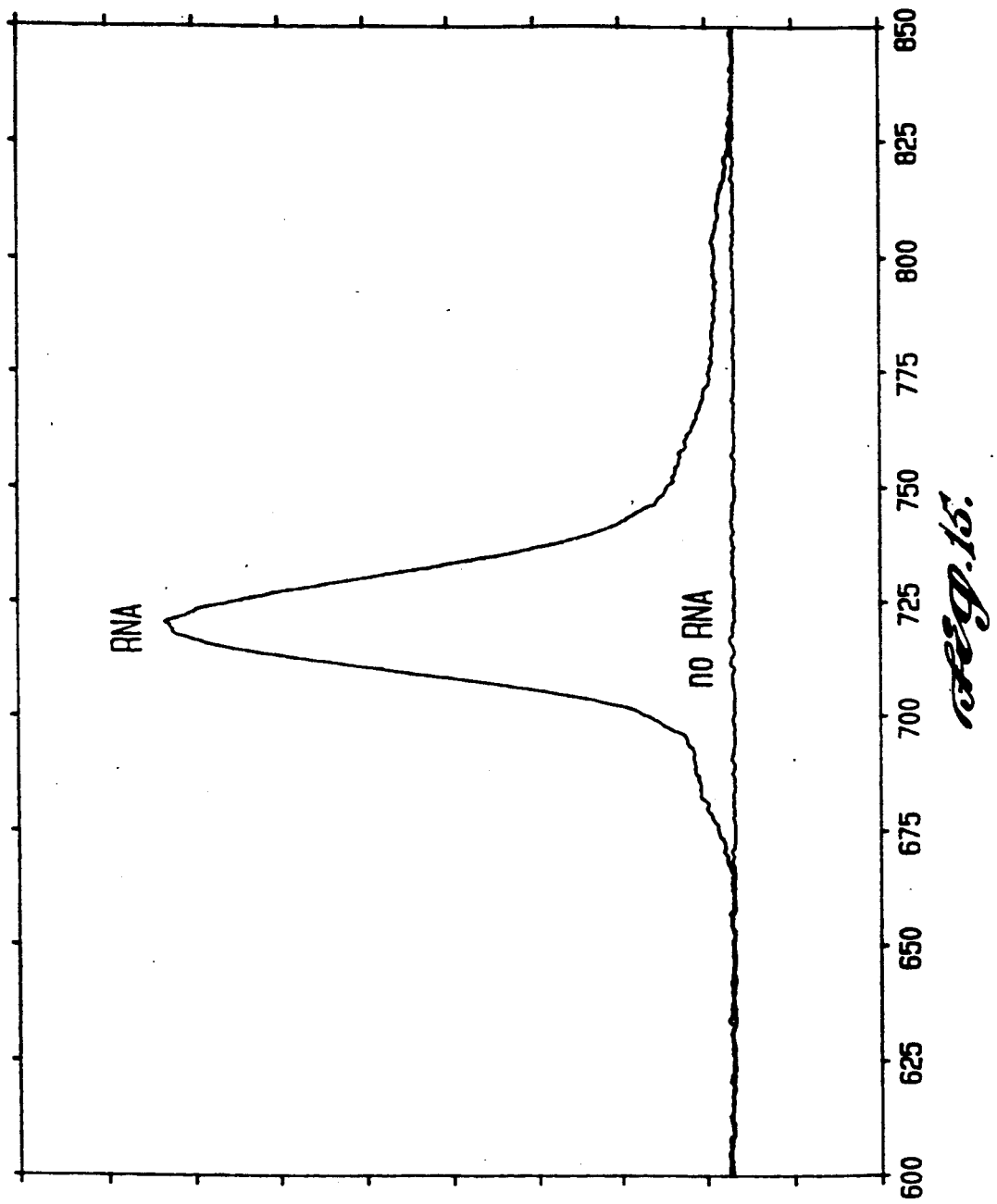
FIG. 15 compares the emission spectra of the metal free phthalocyanine cationic fluorophore, 14a, in water with and without RNA.

The absorbance spectrum of 14a in water presented in FIG. 14 shows nearly complete aggregation. The fluorescence quantum yield is less than 0.01. However, in the presence of RNA (Torula yeast) a strong specific binding interaction occurs which results in the disaggregation of the fluorophore. The absorbance spectrum of 14a in the presence of RNA, FIG. 14, is indicative of a monomeric phthalocyanine. The emission spectra for the two solutions are compared in FIG. 15. The fluorescence enhancement of 14a upon RNA binding is 450-fold.

Figure 16:
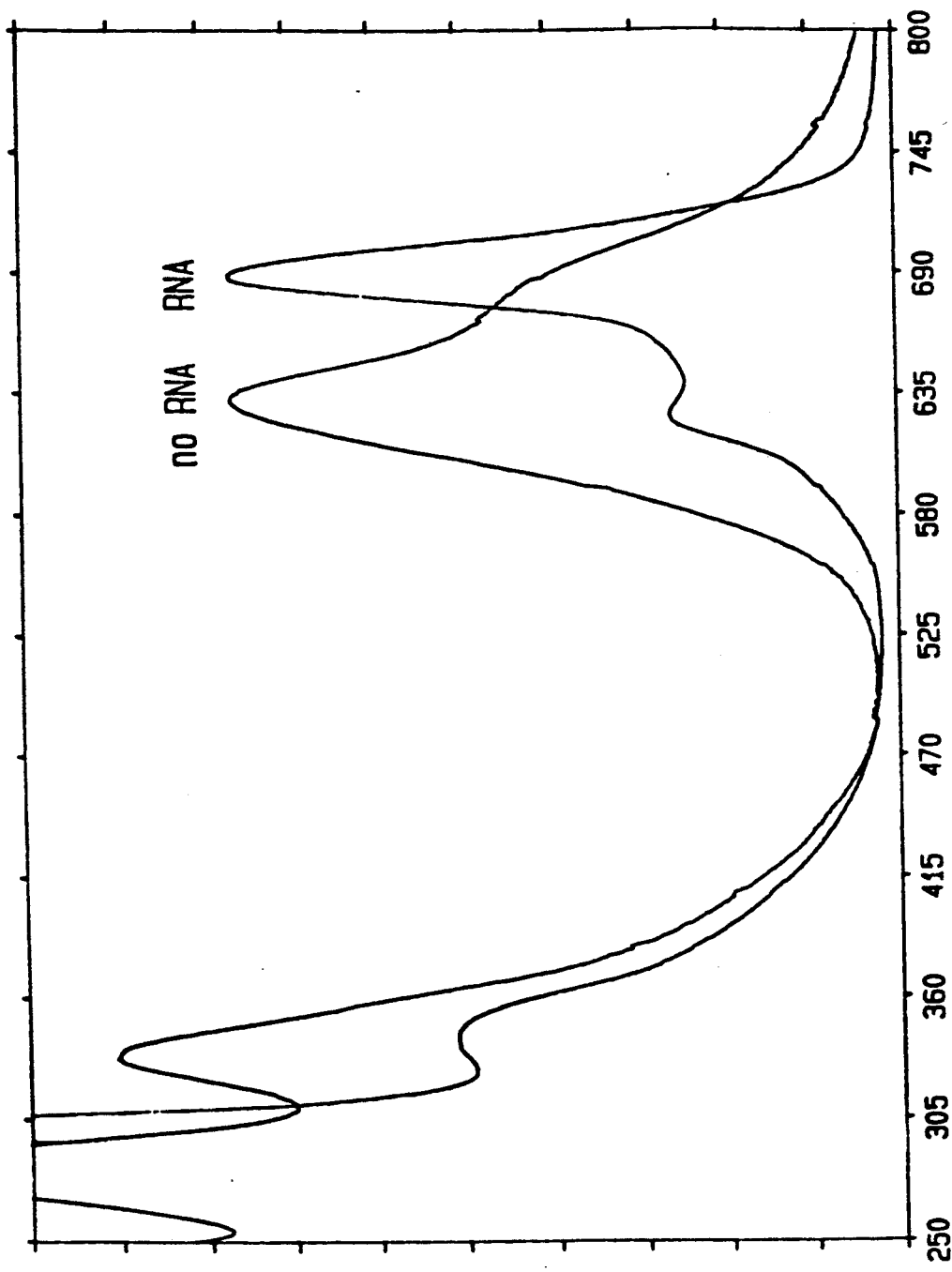
FIG. 16 compares the absorbance spectra of the aluminum phthalocyanine cationic fluorophore, 14b, in water with and without RNA.
Figure 17:
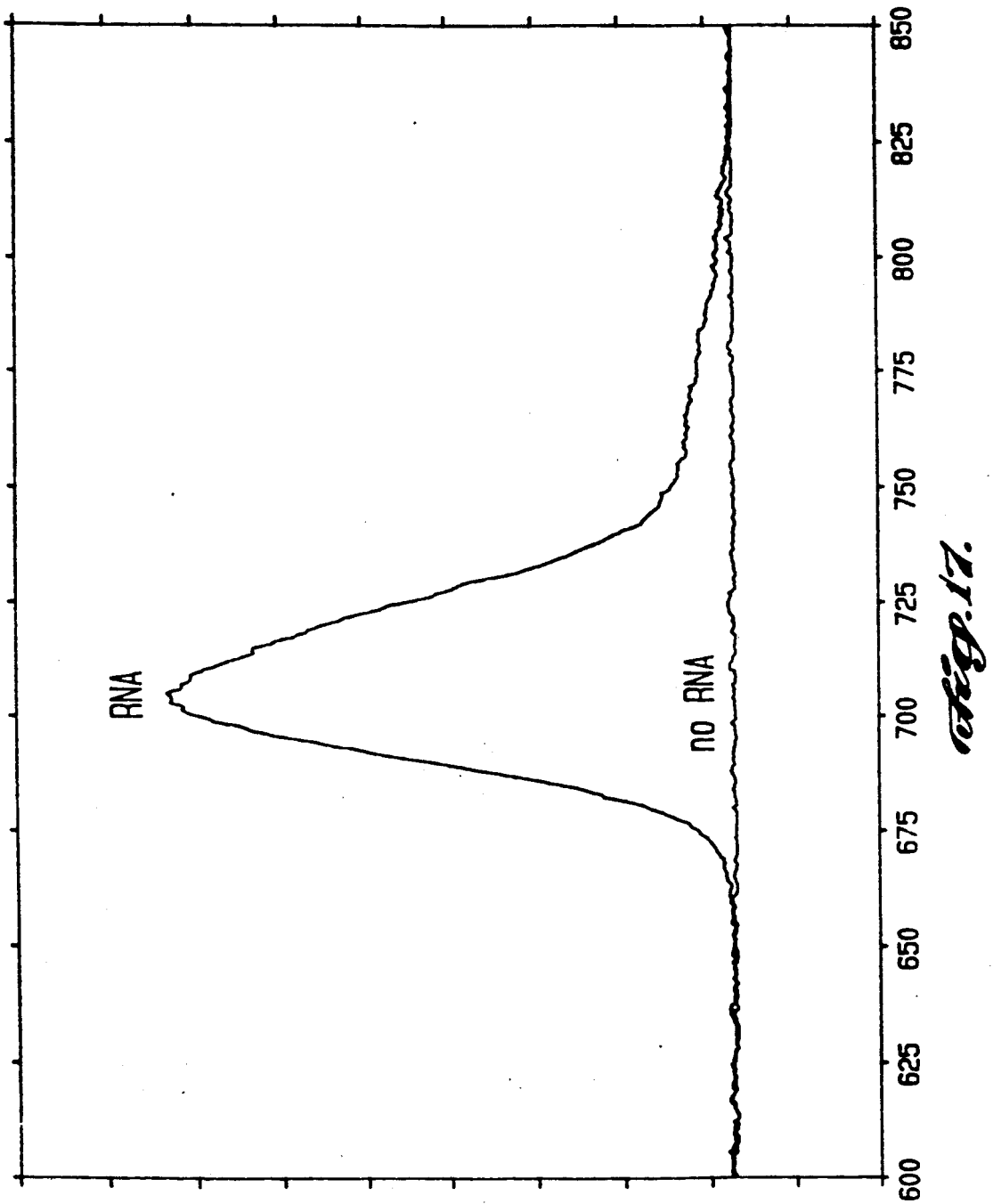
FIG. 17 compares the emission spectra of the aluminum phthalocyanine cationic fluorophore, 14b, in water with and without RNA.

The corresponding absorbance and emission spectra for aluminum derivative 14b are shown in FIGS. 16 and 17, respectively. The fluorescence enhancement upon RNA binding is 340. No fluorescence enhancement was observed for either 14a or 14b in the presence of bovine serum albumin.

Tabulated below are the spectral data for the metal free and aluminum phthalocyanine derivatives prepared as described above. The emission wavelength and fluorescence enhancement of the fluorophores in the presence of RNA are presented. The absorbance data was recorded with a fluorophore concentration of $5 \times 10^{-6}$M and an RNA (Torula Yeast) concentration of 1.0 mg/mL. The fluorescence data was obtained for these solutions at 100-fold dilution.

| Phthalocyanine | Emission Wavelength In Presence of RNA | Fluorescence Enhancement |
|---|---|---|
| Metal free | 720 nm | 450 |
| Aluminum | 705 | 340 |

Another specific embodiment of the cationic phthalocyanines is the case where in formula I M, $R_1$ and $R_2$ are as described above, and X=—$CH_2$—, Y=—$CH_2$C$H_2$— and W=diethylmethylammonium. The counterion is iodide.

EXAMPLE 6

The Preparation of Fluorophore Streptavidin Conjugates

The preparation of covalent streptavidin fluorophore conjugates is described in Example 6. The reactive forms of the red shifted aluminum phthalocyanine derivatives, the sulfonyl chlorides, are coupled to streptavidin according to procedures analogous to those previously disclosed. Schindele, D. C. et al., Monomeric Phthalocyanine Reagents, U.S. patent application Ser. No. 366,971: 1989. The following is a detailed description of the preparations. While the Example explicitly describes coupling to streptavidin, other proteins may be coupled by the same methodology.

Direct Coupling of Aluminum Hydroxy 2,9,16,23-Tetraphenoxyphthalocyanine Sulfonyl Chloride to Streptavidin To 15.0 mg aluminum hydroxy 2,9,16,23-tetraphenoxyphthalocyanine sulfonyl chloride solid was added 300 μL dry dimethylformamide. The solution was placed in a pre-equilibrated 30° C. dry bath. After one hour, 20 μL of the dimethylformamide solution containing the reactive fluorophore was added dropwise to 1.15 mg streptavidin in 185 μL 0.2M sodium bicarbonate in phosphate buffered saline pH adjusted to 9.0 and containing 30 μL dimethylformamide at 4°·C. After one hour, the reaction was quenched by the addition of 250 μL of a 10 mg/mL solution of lysine in 0.2M sodium bicarbonate in phosphate buffered saline containing 0.02% sodium azide as a preservative. After stirring for 30 minutes at 4° C., the conjugate was purified by size exclusion chromatography on Sephadex G-50 in phosphate buffered saline containing 0.02% sodium azide. Spectral data for the conjugate is tabulated below.

Direct Coupling of Aluminum Hydroxy 1,8,15,22-Tetraphenoxyphthalocyanine Sulfonyl Chloride to Streptavidin.

In a procedure analogous to that described above, aluminum hydroxy 1,8,15,22-tetraphenoxyphthalocyanine sulfonyl chloride was coupled to streptavidin. Spectral data for the conjugate is tabulated below.

Direct Coupling of Aluminum Hydroxy 1,8,15,22-Tetrathiophenylphthalocyanine Sulfonyl Chloride to Streptavidin In a procedure analogous to that described above except that a 30 minute incubation at 30° C. was used rather than a one hour incubation, aluminum hydroxy 1,8,15,22-tetraphenoxyphthalocyanine sulfonyl chloride was coupled to streptavidin. Spectral data for the conjugate is tabulated below.

Tabulated below are the absorbance and emission wavelengths for the fluorophore streptavidin conjugates in phosphate buffered saline containing 0.02% sodium azide and prepared as described above. The fluorophore per streptavidin ratio (F/P) was determined by comparing the absorbance of the protein at 280 nm relative to the fluorophore absorbance at 350 nm. The quantum yields reported are per fluorophore.

| Phthalocyanine | Absorbance | Emission | F/P | Quantum Yield |
| --- | --- | --- | --- | --- |
| 2,9,16,23 oxy | 678 nm | 698 nm | 3.7 | 0.35 |
| 1,8,15,22 oxy | 704 | 718 | 2.4 | 0.13 |
| 1,8,15,22 thio | 719 | 729 | 3.6 | 0.03 |

EXAMPLE 7

The Preparation of Fluorophore Labeled Nucleic Acid Primers

The preparation of covalent fluorophore labeled nucleic acid primers is described in Example 7. The reactive forms of the red shifted aluminum phthalocyanine derivatives, sulfonyl chlorides, are coupled to nucleic acid primers according to procedures analogous to those previously disclosed. Schindele, D. C. et al., Monomeric Phthalocyanine Reagents, U.S. patent application Ser. No. 366,971: 1989. The following is a detailed description of the preparations.

Aluminum Hydroxy 2,9,16,23-Tetraphenoxyphthalocyanine Labeled M13mp18 (−21) Universal Sequencing Primer To a stirred solution of 0.022 μmol aminohexane modified M13mp18 (−21), 5' TGTAAAACGACGG-CCAGT 3', Universal sequencing primer in 20 μL 0.5M sodium bicarbonate/0.5M sodium carbonate (pH adjusted to 9.0) was added 1.3 mg aluminum hydroxy 2,9,16,23-tetraphenoxyphthalocyanine sulfonyl chloride in 12 μL dimethylformamide. After stirring overnight at room temperature in the dark, the labeled primer was purified by size exclusion chromatography (Sephadex G-50) followed by polyacrylamide gel electrophoresis. Spectral data for the labeled primer is tabulated below.

Aluminum Hydroxy 1,8,15,22-Tetraphenoxyphthalocyanine Labeled M13mp18 (−21) Universal Sequencing Primer In a procedure analogous to that described above, the primer was labeled with aluminum hydroxy 1,8,15,22-tetraphenoxyphthalocyanine sulfonyl chloride. The primer was purified by ethanol precipitation followed by polyacrylamide gel electrophoresis. Spectral data for the labeled primer are tabulated below.

Tabulated below are the absorbance and emission wavelengths and quantum yields of the aluminum phthalocyanine labeled primers prepared as described above in 0.1M aqueous triethylamine acetate.

| Phthalocyanine | Absorbance | Emission | Quantum Yield |
| --- | --- | --- | --- |
| 2,9,16,23 oxy | 684 nm | 696 nm | 0.39 |
| 1,8,15,22 oxy | 704 | 715 | 0.18 |

EXAMPLE 8

Monofunctional Reactive Tetrabenztriazaporphyrin Derivatives

The 20-substituted tetrabenztriazaporphyrins (TBTAP) described above, like the phthalocyanines, are useful as reagents for fluorescence analysis. One unique property of the TBTAP system is the position 20 substituent. By appropriate selection of the Grignard reagent used in the preparation of the TBTAP (see Examples 3 and 4), a reactive 20-substituent may be synthesized. The Grignard reagent may either contain the functional group of choice or be capable of further elaboration to the group of choice. The resulting 20-substituted TBTAP is then monofunctionally reactive.

Particularly useful reactive groups as $R_2$ enable efficient coupling to biological entities. Preferred reactive groups would include sulfonyl chloride, carboxylic acid and derivatives, amino, isothiocyanate, maleimide, and imidate among others.

An example of a useful monofunctionally reactive TBTAP reagent would be one with an isothiocyanate or N-hydroxysuccinimide ester moiety at position 20. These reagents may be useful in various applications such as immunoassays, nucleic acid sequencing, nucleic acid probe assays, flow cytometry or for selective functionalization. As an example of selective functionalization, the isothiocyanate derivative could serve as a fluorescent reagent in protein sequence analysis utilizing the Edman degradation process. The isothiocyanate portion of the fluorophore couples to the N terminus of the peptide to be sequenced which is immobilized (C terminus) on a solid phase. Degradation of the peptide follows with the fluorophore labeled terminal amino acid being cleaved from the peptide. The fluorophore labeled amino acid is then removed from the immobilized peptide and the amino acid is identified. The new N terminus of the remaining peptide, now one amino acid residue shorter, is ready for the next cycle. Repetition of the process results in the sequential identification of the amino acid residues of the peptide of interest. Highly fluorescent reagents, such as phthalocyanines and TBTAPs, would improve the detection limits of protein sequence analysis and enable the sequencing of smaller quantities of protein. The advantage of highly sensitive fluorophores is particularly relevant when only trace quantities of rare proteins are available.

EXAMPLE 9

Monofunctional Wavelength Modified Tetrabenztriazaporphyrin Derivatives

The 20-substituent of the TBTAP ring system may be designed to create the desired optical properties of the TBTAP. As with peripheral ring substitution detailed above in Examples 2 and 3, the wavelengths of absorbance and fluorescent emission may be manipulated by the choice of substituent at position 20. Electron donating groups are expected to red shift both absorbance and fluorescence wavelengths while a blue shift is anticipated for electron withdrawing groups.

Fluorinated 20-substituted TBTAP derivatives such as trifluoromethyl ($CF_3$) and perfluorophenyl ($C_6F_5$) may be prepared from commercially available 1,1,1-trifluoro-2-bromoethane and 2,3,4,5,6-pentafluorobenzyl bromide, respectively. These TBTAP bearing electron withdrawing substituents are predicted to absorb and emit light at wavelengths blue of the parent.

EXAMPLE 10

Phthalocyanine and Tetrabenztriazapophyrin Derivatives Bearing Substituted Phenyl Groups The tetrasubstituted phthalocyanines and tetrabenztriazaporphyrins described in Examples 2 and 3 are derived from unsubstituted phenoxy or thiophenylphthalonitriles. Substituted phenoxy or thiophenylphthalonitriles may also be prepared and cyclized to the corresponding phthalocyanines or tetrabenztriazaporphyrin systems. These modified derivatives may serve to fine tune the optical properties of the parent tetrasubstituted material.

For example, 3-(4-fluorophenoxy)phthalonitrile may be prepared by treatment of 4-fluorophenol with 3-nitrophthalonitrile in a procedure analogous to that which results in the production of 3-phenoxyphthalonitrile. Cyclization of the fluoro substituted phthalonitrile to the phthalocyanine or TBTAP, will result in the formation of a species slightly different from its non-fluorinated parent. The optical properties will also vary slightly from the parent.

Many substituted phenols and thiophenols are known. By the methodology described above, many substituted derivatives of tetraphenoxy- and tetrathiophenylphthalocyanines and TBTAPs may be prepared.

EXAMPLE 11

Octasubstituted Phthalocyanine and Tetrabenztriazaporphyrin Derivatives

Octasubstituted phthalocyanines and tetrabenztriazaporphyrins may be prepared from disubstituted phthalonitriles in procedures analogous to those described in Examples 2 and 3 for the preparation of tetrasubstituted phthalocyanines and TBTAPs from monosubstituted phthalonitriles. The octasubstituted derivatives may be broadly categorized based on the position of the substitution. Symmetrical phthalocyanines and TBTAPs are derived from 3,6- and 4,5-disubstituted phthalonitriles. Less symmetrical and more difficult to prepare are 3,4- and 3,5-disubstituted phthalonitriles.

Octaoxy and octathiophthalocyanines derived from 3,6- and 4,5-disubstituted phthalonitriles have been reported. 3,6-octaoxy: Witkiewicz, Z. et al., Materials Science II, 1:39–45 (1976). 4,5-octaoxy: Metz, J., et al., Inorg. Chem., 23:1065–1071 (1984). 3,6- and 4,5-octathio: Oksengendler, I. G. et al., J. Org. Chem. USSR, 14(5): 1046–1051 (1978). The sulfur substituted derivatives absorb at greater wavelengths than the oxygen analogs.

We tabulate below the spectral properties of aluminum 3,6-octamethoxy and 4,5-octamethoxyphthalocyanine. The absorbance and emission wavelengths and quantum yields were recorded in dimethylformamide solution.

| Phthalocyanine | Absorbance | Emission | Quantum Yield |
| --- | --- | --- | --- |
| 3,6-octamethoxy | 739 nm | 748 nm | 0.02 |
| 4,5-octamethoxy | 672 | 678 | 0.21 |

The 3,6-methoxy derivative exhibits a significant red shift. However, the fluorescence quantum yield is low. The 4,5-methoxy derivative is actually blue shifted and retains more of a fluorescence emission. Both of these derivatives may be further elaborated to water soluble and reactive reagents by a reaction sequence completely analogous to that described for the isomeric aluminum tetraneopentoxyphthalocyanines described in Example 1.

Octasubstituted derivatives composed of four sulfur substituents and four oxygen substituents may also be prepared as described in the Examples above. These derivatives may be prepared from phthalonitriles substituted with both an oxygen and a sulfur substituent, for example, 3-thiophenyl-5-phenoxyphthalonitrile. The phenyl groups in the example may be other than phenyl and the position of the substituents may also vary. The optical properties of these mixed derivatives is expected to be intermediate between the octaoxy and the octathio analogs.

4,5-Octasubstituted carbon derivatives may also be prepared. In the case where the 4,5-substituent is a benzo ring, the system is known as a naphthalocyanine. These highly conjugated derivatives are approximately 100 nm red shifted relative to their phthalocyanine counterparts. Vogler, A. and H. Kunkely, Inorganica Chimica Acta, 44:L209–L210 (1980). Tabulated below are the spectral characteristics of aluminum phthalocyanine and naphthalocyanine chlorides in dimethylformamide.

|  | Absorbance | Emission | Quantum Yield |
| --- | --- | --- | --- |
| Phthalocyanine | 671 nm | 672 nm | 0.60 |
| Naphthalocyanine | 768 | 770 | 0.11 |

EXAMPLE 12

Pyrazine Porphyrazines

Closely related in structure to phthalocyanines are pyrazine porphyrazines. Linstead, R. P. et al., J. Chem. Soc. 911–921, 1937. Phthalocyanines bear four benzo rings appended to the macrocycle while pyrazine porphyrazines have four pyrazine (1,4-diazabenzene) rings.

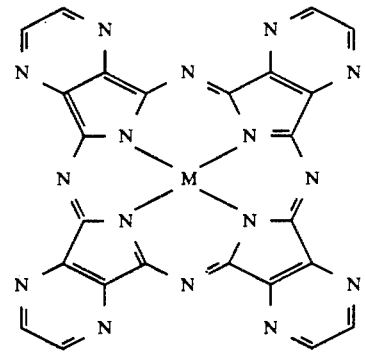

Elaboration of tetra- and octaphenylpyrazine porphyrazine to reactive, and water soluble aluminum derivatives is the subject of Example 12. Cyclization of either 5-phenyl or 5,6-diphenylpyrazine 2,3-dinitrile results in the porphyrazine macrocycle. Metalation with aluminum chloride in quinoline provides the corresponding aluminum derivatives. Treatment with chlorosulfonic acid gave the reactive intermediates and hydrolysis of these produced the water soluble aluminum pyrazine porphyrazine sulfonates. Tabulated below are the spectral data for aluminum tetra and octaphenylpyrazine porphyrazine sulfonates in water.

| Pyrazine Porphyrazine | Absorbance | Emission | Quantum Yield |
| --- | --- | --- | --- |
| tetraphenyl (pH 10) | 641 nm | 647 nm | 0.17 |
| octaphenyl | 651 | 654 | 0.95 |

EXAMPLE 13

Pyridine Porphyrazines

Closely related in structure to phthalocyanines are pyridine porphyrazines. Linstead, R. P., et al., J. Chem.

Soc. 911–921, 1937. Structurally, replacement of the benzo ring in phthalocyanine with pyridine gives pyridine porphyrazine.

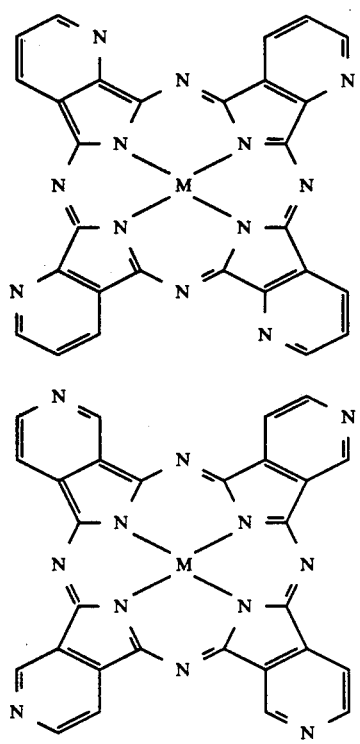

These derivatives may be prepared from either 2,3-dicyanopyridine or 3,4-dicyanopyridine. Cyclization of 2,3-dicyanopyridine gives 3-pyridine porphyrazine while 3,4-dicyanopyridine produces 4-pyridine porphyrazine. Like pyrazine porphyrazines, the pyridine porphyrazines absorb at wavelengths blue-shifted relative to phthalocyanines, with the 3-pyridine isomer blue-shifted relative to the 4-pyridine porphyrazine. Metalation with aluminum chloride in quinoline provided the aluminum derivatives.

Application of the oxygen and sulfur substitution methodology developed for the phthalocyanines and tetrabenztriazaporphyrins as described in Examples 2 and 3, respectively, will result in a family of reagents for each of the aluminum pyridine porphyrazines.

EXAMPLE 14

Imaging and Radionuclide Reagents

The reagents of this invention are organometallic compounds and as such many different metals may be bound. The macrocyclic ring systems disclosed are capable of efficient chelation of a variety of metals useful in image analysis and therapeutic applications, such as magnetic resonance imaging, radionuclide imaging, and as radiopharmaceuticals. Active metals for these applications may be incorporated into the macrocycle and directed to the site of interest. The targeting of the metal bearing reagent may be a naturally selective uptake of the reagent by the site of interest, an antibody directed against an antigen present at the site of interest to which the reagent is conjugated, a complementary fragment of DNA to which the reagent is coupled, a membrane probe to which the reagent is coupled or some other delivery mechanism.

Paramagnetic metals useful for magnetic resonance imaging contrast agents include gadolinium, manganese, and iron.

The field of nuclear medicine utilizes radioisotopes, usually gamma-emitting isotopes, for diagnostic purposes. Radioactive metal complexes of copper 67, technetium 99, cobalt 57, and gallium 67 have been used as radiopharmaceuticals in both diagnostic and therapeutic applications.

The reagents of this invention may be useful in the applications described above by virtue of their metal binding capabilities. Also, the biological conjugates of this invention will serve to act as targeting agents for the applications described above.

Representative malignancies that can be treated by the radionuclides are: leukemia, ovarian cancer, lymphoma, breast cancer, myeloma, kidney, liver, and colorectal cancer, and the like.

EXAMPLE 15

Improved Photodynamic Therapeutic (PDT) Reagents

PDT agents (photosensitizers) are selectively taken up by cancerous tissue and upon irradiation with visible light become activated. The activated photosensitizers effectively kill cells in their immediate vicinity presumably by the generation of singlet oxygen. Spikes, J. D., Photochem. Photobiol. 43(6)691–699 (1986). The reagents of this invention offer two improvements over the existing technology. The first advantage lies in the deep red absorbance of the disclosed reagents and the second in the targeting of these reagents made possible by their biological binding conjugates.

Phthalocyanines and TBTAPs which absorb in the deep red with large molar absorptivities will enable treatment of more tissue. Currently PDT reagents are limited by their relatively blue absorbance profiles with respect to depth of penetration of activating light. Since human tissue is nearly transparent in the near infrared, PDT agents which absorb in this region will be most effective. The utilization of red-shifted phthalocyanines and TBTAPs will enable access to tissues which would be unaffected by currently employed blue absorbing sensitizers.

The targeting of the photosensitizer is a critical aspect in PDT. Today, the natural selectivity of photosensitizers for tumorous tissue is the most commonly relied upon delivery mechanism. The reagents of this invention, by virtue of their conjugation to biological entities such as antibodies or oligonucleotides, can seek out and bind to sites requiring photodynamic treatment. The conjugation of these deep red absorbing phthalocyanines and TBTAPs to antibodies (or antigen binding antibody fragments) directed against cancerous tissue or cancer-associated antigens enables efficient delivery of the photoactivatable agents to the cancer. Alternatively, the coupling of red absorbing phthalocyanines and TBTAPs to a complementary fragment of DNA enables the use of anti-sense oligonucleotides or DNA probes as targeting agents. Another targeting method involves covalently attaching the reagent to a membrane probe, as defined above.

Representative malignancies that could be treated by PDT using the present reagents are: bladder cancer, skin cancer (melanoma), esophogeal cancer, brain tumors, other solid tumors, and the like.

EXAMPLE 16

A representative example of a two color system for AIDS testing that employs the phthalocyanine based fluorophores is as follows. Anti-CD4 (helper T cell specific monoclonal antibody) labeled with phthalocyanine (I) where $R_2$ is antibody-$SO_2$—, Z=N, two $R_1$ groups are —$SO_3^-$ the third $R_1$ group is hydrogen (Dye I) and anti-CD8 (suppressor T cell specific monoclonal antibody) labeled with phthalocyanine (I) where $R_2$ is antibody-$SO_2$—phenyl-O, each $R^1$ is XYW, wherein X=O, Y=phenyl, W=—$SO_3^-$. The $R_1$ and $R_2$ group, are located at the 1, 8, 15, 22 positions. (3 isomer, Dye III) are incubated with peripheral blood lymphocytes. During this incubation, anti-CD4-Dye I binds to helper cells and anti-CD8-Dye III binds to the suppressor cells. Since the T helper cells are labeled with a fluorophore that emits at one wavelength (Dye I) and the T suppressor cells are labeled with a fluorophore that emits at a different wavelength (Dye III) that is both resolved and red-shifted from that on the helper cells, each subset of cells may be quantitated simultaneously using a flow cytometer equipped with optical filters that allow for discrimination of the two different fluorophores.

While the present invention has been described in conjunction with preferred embodiments and illustrative examples, one of ordinary skill after reading the foregoing specification will be able to effect various changes, substitutions of equivalents, and other alternations to the reagents, methods, and kits set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A reagent having the formula:

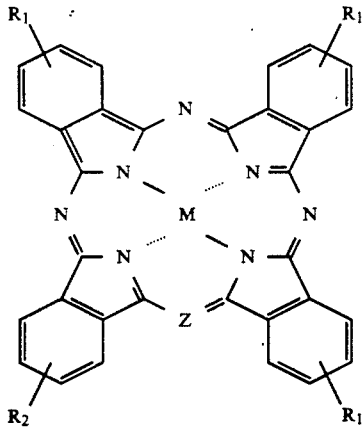

wherein
M is selected from the group consisting of $H_2$, aluminium, silicon, phosphorus, gallium, germanium, cadmium, scandium, magnesium, tin, and zinc;
each $R_1$ is independently —XYW, —YW, —W, or hydrogen;
X is oxygen, nitrogen, sulfur, phosphorus, silicon, or selenium; or X is $CR_3R_4$, wherein $R_3$ and $R_4$ are independently selected from the group consisting of hydrogen, alkyl, aryl, and aralkyl, or $R_3$ and $R_4$ together form a carbonyl oxygen; or X is phenyl;
Y is a linking group between X and W when $R_1$ is —XYW, or between W and an aromatic ring of said reagent when $R_1$ is —YW;
W is a water-soluble group;
$R_2$ is —A or —Y'A, wherein —A is a biological entity and Y' is a linking group to —A; or $R_2$ is reactive or activatable group; and
Z is —CR, where —R is H, alkyl, aryl, or aralkyl.

2. A reagent according to claim 1, wherein $R_1$ is —XYW or —YW and wherein Y is a $C_1$-$C_7$ saturated or unsaturated, straight chain, branched, or cyclic hydrocarbon moiety.

3. A reagent according to claim 1, wherein $R_1$ is —XYW or —YW and wherein Y is a polyether, polyamine, polyalcohol, sugar, peptide, or nucleotide.

4. A reagent according to claim 1, wherein W is —OH, —$CO_2H$, —$OCH_2CO_2H$, —$PO_4^=$, —$PO_3^-$, —$SO_3^-$, —$SO_2^-$, —$SO_2Cl$, —$SO_4^=$, —$NH_2$, —NHD, —$NHD_1D_2$, or —$N^+D_1D_2D_3$, wherein D, $D_1$, $D_2$, and $D_3$ are independently $C_1$-$C_{10}$ alkyl, $C_6$-$C_{12}$ aryl, or $C_6$-$C_{12}$ aralkyl.

5. A reagent according to claim 1, wherein $R_1$ is —XYW or —YW and wherein Y is $C_1$-$C_3$ alkylene and W is sulfonate or carboxylate.

6. A reagent according to claim 5, wherein —XYW is substituted at 1-4 of the 1, 8, 15, and 22 positions on the macrocycle.

7. A reagent according to claim 5, wherein —XYW is substituted at 1-4 of the 2, 9, 16, and 23 positions on the macrocycle.

8. A reagent according to claim 1, wherein M is aluminum, and at least one $R_1$ is —XYW, wherein X is O or S, and W is sulfonate or sulfonyl chloride.

9. A reagent according to claim 8, wherein Y is phenyl.

10. A reagent according to claim 1, comprising
2, 9, 16, 23 tetraphenoxy aluminum 20-phenyl tetrabenztriazaporphyrin,
1, 8, 15, 22 tetraphenoxy aluminum 20-phenyl tetrabenztriazaporphyrin, or
1, 8, 15, 22 tetrathiophenyl aluminum 20-phenyl tetrabenztriazaporphyrin, linked to $R_2$.

11. A reagent according to claim 1, wherein $R_2$ is —A or —Y'A, and wherein A is a nucleic acid selected from the group consisting of ATP, CTP, GTP, TTP, UTP, dATP, dCTP, dGTP, dTTP, dUTP, ddATP, ddCTP, ddGTP, ddTTP, ddUTP, and derivatives thereof, oligonucleotides, and polynucleotides.

12. A kit for sequencing DNA, comprising:
a plurality of containers, each containing a different reagent according to claim 1,
wherein the different reagents are characterized by having a common excitation wavelength and different wavelengths of maximum emission.

13. A kit according to claim 12, wherein there are four reagents, and wherein each $R_2$ group comprises a different nucleotide, deoxynucleotide, or dideoxynucleotide.

14. A reagent according to claim 1, wherein M is aluminum, each $R_1$ is sulfonate, and Z is C-phenyl, attached to $R_2$.

15. A reagent having the formula:

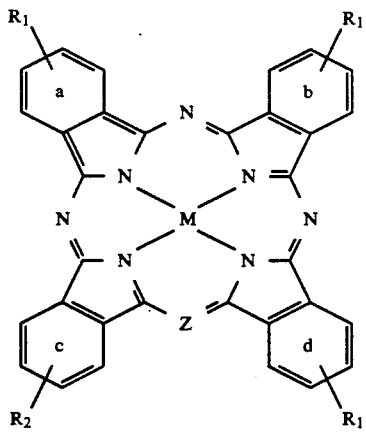

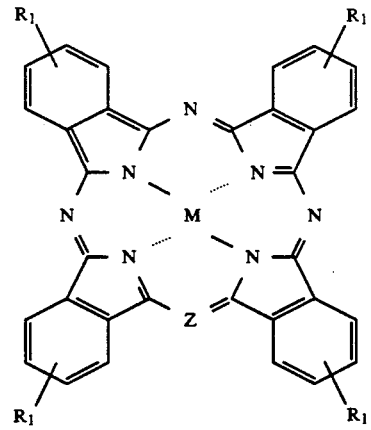

wherein
- M is selected from the group consisting of H₂, aluminum, silicon, phosphorus, gallium, germanium, cadmium, scandium, magnesium, tin, and zinc;
- each $R_1$ is independently —XYW, —YW, —W, or hydrogen;
- X is oxygen, nitrogen, sulfur, phosphorus, silicon, or selenium; or X is $CR_3R_4$, wherein $R_3$ and $R_4$ are independently selected from the group consisting of hydrogen, alkyl, aryl, and aralkyl, or $R_3$ and $R_4$ together form a carbonyl oxygen; or X is phenyl;
- Y is a linking group between X and W when $R_1$ is —XYW, or between W and an aromatic ring of said reagent when $R_1$ is —YW;
- W is a water-soluble group;
- $R_2$ is —A or —Y'A, wherein —A is a biological entity and Y' is a linking group to —A;
- Z is nitrogen or —CR, wherein —R is H, alkyl, aryl, or aralkyl; and wherein at least one of the benzo rings a, b, c, and d depicted in the formula above is a pyridine or pyrazine ring.

16. A reagent having the formula:

wherein
- M is selected from the group consisting of H₂, aluminum, silicon, phosphorus, gallium, germanium, cadmium, scandium, magnesium, tin, and zinc;
- each $R_1$ is independently —XYW, —YW, —W, or hydrogen;
- X is oxygen, nitrogen, sulfur, phosphorus, silicon, or selenium; or X is $CR_3R_4$, wherein $R_3$ and $R_4$ are independently selected from the group consisting of hydrogen, alkyl, aryl, and aralkyl, or $R_3$ and $R_4$ together form a carbonyl oxygen; or X is phenyl;
- Y is a linking group between X and W when $R_1$ is —XYW, or between W and an aromatic ring of said reagent when $R_1$ is —YW;
- W is a water-soluble group; and
- Z is —C—$R_2$, wherein $R_2$ is —A is or —Y'A, wherein is —A is a biological entity and Y' is a linking group to —A; or $R_2$ is a reactive or activatable group suitable for conjugating to a biological entity without substantially impairing the fluorescence of the reagent or the biological activity of the biological reagent.

* * * * *

UNITED STATES PATENT AND TRADEMARK OFFICE
CERTIFICATE OF CORRECTION

PATENT NO. : 5,135,717

DATED : August 4, 1992

INVENTOR(S) : G. E. Renzoni et al.

It is certified that error appears in the above-identified patent and that said Letters Patent is hereby corrected as shown below:

| COLUMN | LINE | |
|---|---|---|
| Item [54] and col. 1 | 1-3 2-3 | "TETRABENZTRIAZAPORPHYRIN REAGENTS AND KITS CONTAINING THE SAME" should read --PHTHALOCYANINE AND TETRABENZTRIAZAPORPHYRIN REAGENTS AND KITS CONTAINING THE SAME-- |
| [56] ("Other Publications") | 16th Ref. | "Hasiguchi" should read --Hashiguchi-- |
| [56] ("Other Publications") | 19th Ref. | "distributed" should read --distribution-- |
| 2 | 18 | "chlorsulfonation" should read --chlorosulfonation-- |
| 8 | 37 | "solubizing" should read --solubilizing-- |
| 9 | 61 | "membrance" should read --membrane-- |
| 9 | 63 | "membrance" should read --membrane-- |
| 11 | 34 | "above" should read --above,-- |
| 12 | 19 & 20 | "tetrabenz-triazaporhphrins" should read --tetrabenztriaza-porphyrins-- |
| 18 | 46 | "fluorophorelabeled" should read --fluorophore-labeled-- |
| 25 | 64 | "hour." should read --hours.-- |

UNITED STATES PATENT AND TRADEMARK OFFICE
CERTIFICATE OF CORRECTION

PATENT NO. : 5,135,717

DATED : August 4, 1992

INVENTOR(S) : G. E. Renzoni et al.

It is certified that error appears in the above-identified patent and that said Letters Patent is hereby corrected as shown below:

| | | |
|---|---|---|
| 27 | 20 | "drived" should read --dried-- |
| 30 | 54 | "hour." should read --hours.-- |
| 31 | 14 | "Example 5The" should read --Example 5. The-- |
| 39 | 15 | after "to" insert --the-- |
| 39 (Claim 1, | 61 & 62 Lines 20 & 21) | "alu-minium" should read --aluminum-- |
| 40 (Claim 1, | 8 Line 35) | after "R$_2$ is" insert --a-- |
| 40 (Claim 10, | 44 & 45 Line 5) | after "tet-rabenztriazaporphyrin," insert --2, 9, 16, 23 tetrathiophenyl aluminum 20-phenyl tetrabenztriazaporphyrin,-- |
| 42 (Claim 16, | 35 Line 36) | after "-A" delete "is" |

Signed and Sealed this

Twenty-ninth Day of March, 1994

Attest:

BRUCE LEHMAN

Attesting Officer      Commissioner of Patents and Trademarks